(12) United States Patent
Masure et al.

(10) Patent No.: US 7,425,327 B2
(45) Date of Patent: Sep. 16, 2008

(54) CHOLINE BINDING PROTEINS FOR ANTI-PNEUMOCOCCAL VACCINES

(75) Inventors: H. Robert Masure, Germantown, TN (US); Carsten I. Rosenow, New York, NY (US); Elaine Tuomanen, Germantown, TN (US); Theresa M. Wizemann, Germantown, MD (US)

(73) Assignee: The Rockefeller University, New York, NY (US)

( * ) Notice: Subject to any disclaimer, the term of this patent is extended or adjusted under 35 U.S.C. 154(b) by 575 days.

(21) Appl. No.: 10/901,305

(22) Filed: Jul. 28, 2004

(65) Prior Publication Data

US 2005/0048590 A1 Mar. 3, 2005

Related U.S. Application Data

(60) Continuation of application No. 09/829,382, filed on Apr. 9, 2001, now Pat. No. 6,784,164, which is a division of application No. 08/847,065, filed on May 1, 1997, now Pat. No. 6,245,335.

(60) Provisional application No. 60/016,632, filed on May 1, 1996.

(51) Int. Cl.
*A61K 39/395* (2006.01)
*C07K 16/00* (2006.01)
*C12N 5/06* (2006.01)
*C12N 5/16* (2006.01)

(52) U.S. Cl. .................... 424/130.1; 435/326; 435/331; 530/387.1; 530/388.1

(58) Field of Classification Search ............... 424/130.1; 435/326, 331; 530/387.1, 388.1
See application file for complete search history.

(56) References Cited

FOREIGN PATENT DOCUMENTS

| EP | 622081 | 11/1994 |
|---|---|---|
| WO | WO 93/14198 | 7/1993 |
| WO | WO 93/24000 | 12/1993 |
| WO | WO 95/06732 | 3/1995 |
| WO | WO 96/40928 | 12/1996 |
| WO | WO 97/09994 | 3/1997 |
| WO | WO 97/41151 | 11/1997 |

OTHER PUBLICATIONS

Barril et al. (1994) Gene 142:91-6.
Briese and Hakenback *Eur. J. Biochem.* 146:417-427.
Diaz et al. (1989) J. Biol. Chem. 264:1238-44.
Diaz et al. (1990) Gene 90:157-62.
Diaz et al., *J. Bacteriol.* 174:5516-25 (1992).
Hoepelman and Tuomanen, *Infect. Immun.*, 60:1729-33 (1992).
Leyva-Vazquez et al. (1994) 176:3903-10.
Pearce et al., *Mol. Microbiol.*, 9:1037-50 (1993).
Pearce et al., 1992, *Abstr. Gen. Meet. Am. Soc. Microbiol.* 92:127, D-188.
Romero et al., *Microb. Lett.* 108:87-92 (1993).
Ronda et al., *Eur. J. Biochem.* 164:621-4 (1987).
Rosenow, C.I. (1996) 96th ASM General Meeting, New Orleans, Abstract.
Sanchez-Beato, et al., *J. Bacteriol.* 177:1098-1103 (1995).
Sanchez-Beato et al *J. of Bacteriol.* 177:1098-1103.
Sanchez-Puelles et al *Gene* 89:69-75 (1990).
Sun et al. (1988) Antimicrob. Agents Chemother. 32:1370-4.
Talkington et al., *Microb. Pathog.* 13:343-355 (1992).
van der Flier et al., *Infect. Immun.*, 63:4317-4322, (1995).
Von Eichel-Streiber and Sauerborn, *Gene* 96:107-13 (1990).
Von Eichel-Streiber et al., *J. Bacteriol.* 174:6707-6710 (1992).
Wren *Micro. Review Mol. Microbiol.* 5:797-803 (1991).
Yother and White *J. of Bacteriol.* 176:2976-2985.
Yother et al., *J. Bacteriol.*, 174:610 (1992).
Garcia et al. (1989) Biochem. Biophys. Res. Comm. 158:251-6.
Garcia et al. (1987) J. Virol. 61:2573-80.
Hames et al. eds., In: Gel Electroph. Prot. IRL, Washinton DC, pp. 265-277.
Lehninger (1975) Biochemistry, 2nd ed., Worth Publishers, NY, p. 430.
Webster's II New Riverside Dictionary, Boston, Houghton Mifflin, p. 589.
Garcia et al., J of Virology, 61(8): 2573-80, 1987.
Brooks-Walter et al., 1999, Infection and Immunity 67(12):6533-42.
Pedro Garcia et al., 1999, MicroCorrespondence, Molecular Microbiology, 31(4):1275-81.
Pedro Garcia et al., 1999, Molecular Microbiology, 33(1):128-138.
Hammerschmidt et al., 1997, Molecular Microbiology 25:1113-24.

*Primary Examiner*—Mark Navarro
(74) *Attorney, Agent, or Firm*—Klauber & Jackson LLC

(57) ABSTRACT

The invention relates to bacterial choline binding proteins (CBPs) which bind choline. Such proteins are particularly desirable for vaccines against appropriate strains of Gram positive bacteria, particularly *streptococcus*, and more particularly *pneumococcus*. Also provided are DNA sequences encoding the bacterial choline binding proteins or fragment thereof, antibodies to the bacterial choline binding proteins, pharmaceutical compositions comprising the bacterial choline binding proteins, antibodies to the bacterial choline binding proteins suitable for use in passive immunization, and small molecule inhibitors of choline binding protein mediated adhesion. Methods for diagnosing the presence of the bacterial choline binding protein, or of the bacteria, are also provided. In a specific embodiment, a streptococcal choline binding protein is an enolase, which demonstrates strong affinity for fibronectin.

6 Claims, 18 Drawing Sheets

6% SDS-PAGE

FIG. 10

Amino terminal sequencing of 50 kDa protein:

S. pneumoniae 2    ITDVYAREVLDSRGNP    17
                   I DV AREVLDSRGNP
B. subtilis enolase 5    IVDVRAREVLDSRGNP    20

FIG. 14

```
1     TCCCGGGCAACCCAACACTTGAAGTAGAAGTTTACACTGAATCAGGTGCTTCGGACGT    60
2447  TCCCGGGCAACCCAACAGTTGAAGTTGAAGTATACAGAAACAGGAGAGCTTCGGCCGC    2506

61    GGTATGGTTCCATCAGGAGCTTCTACTGGTGAACACGAAGCAGTTGAACTTCGCGACGGT    120
2507  GCATTAGTGCCAAGCGGAGCTTCTACAGGTCAATACGAAGCGGTTGAGCTTCGTGACGGC    2566

121   GACAAATCTCGTTACGGTGGTCTTGGTACACAAAAGCTGTTGACAACGTAAACAACATC    180
2567  GACAAAGACCGTTACCTTGGAAAGGGCGTGTTAACAGCTGTAACAACGTAAACGAAATC    2626

181   ATTGCTGAGGCCATCATTGGCACGATGTA    210   S. pneumoniae
2627  ATTGCTCCAGAGCTTCTTGGCTTTGATGTA    2656  B. subtilis
```

FIG. 15

| | | | |
|---|---|---|---|
| S. pneumoniae | 1 | SRGNPTLEVEVYTESGAFGRGMVPS | 25 |
| B. subtilis | 15 | SRGNPT+EVEVYTE+GAFGR +VPS<br>SRGNPTVEVEVYTETGAFGR A LVPS | 39 |
| S. pneumoniae | 26 | GASTGEHEAVELRDGDKSRYGGLGT | 50 |
| B. subtilis | 40 | GASTG ++ EAVELRDGDK RY G G<br>GASTGQYEAVELRDGDKDRYLGKGV | 64 |
| S. pneumoniae | 51 | QKAVDNVNNI IAEAI IGYDV | 70 |
| B. subtilis | 65 | AV +NVN IIA ++ G+DV<br>LTAVN NVNEI IAPELLGFDV | 84 |

CHOLINE BINDING PROTEINS FOR ANTI-PNEUMOCOCCAL VACCINES

CROSS-REFERENCE TO RELATED APPLICATIONS

This application is a Continuation Application of U.S. Ser. No. 09/829,382, filed Apr. 9, 2001, now U.S. Pat. No. 6,784,164, which is a Divisional of U.S. Ser. No. 08/847,065, filed May 1, 1997, now U.S. Pat. No. 6,245,335, which is a non-provisional application claiming priority to Provisional Application Ser. No. 60/016,632, filed May 1, 1996. Applicants claim the benefit of these applications under 35 U.S.C. §120, and 35 U.S.C. §119(e), the contents all of which are incorporated herein by reference in their entireties.

The present application claims priority to Provisional Patent Application Ser. No. 60/016,632, filed May 1, 1996, pursuant to 35 USC 119(e), the disclosure of which is incorporated herein by reference in its entirety.

The research leading to the present invention was supported, in part, by Grant Nos. AI 36445 and AI 38446 from the National Institutes of Health. Accordingly, the Government may have certain rights in the invention.

FIELD OF THE INVENTION

The present invention relates generally to choline binding proteins, methods for isolating choline binding proteins, and the genes encoding such proteins. The invention also relates to acellular vaccines to provide protection from bacterial infection using such proteins, and to antibodies against such proteins for use in diagnosis and passive immune therapy. In particular, the choline binding proteins of the invention are useful as vaccines against pneumococcus. Where a choline binding protein demonstrates activity as an adhesion protein, it is also useful as a competitive inhibitor of bacterial adhesion, or to discover small molecule antagonists of adhesion.

BACKGROUND OF THE INVENTION

Antibacterial Vaccine Strategies

Exported proteins in bacteria participate in many diverse and essential cell functions such as motility, signal transduction, macromolecular transport and assembly, and the acquisition of essential nutrients. For pathogenic bacteria, many exported proteins are virulence determinants that function as adhesions to colonize and thus infect the host or as toxins to protect the bacteria against the host's immune system [International Patent Publication No. WO 95/06732, published Mar. 9, 1995 by Masure et al., which is specifically incorporated herein by reference in its entirety, for a review, see Hoepelman and Tuomanen, *Infect. Immun.*, 60:1729-33 (1992)]. However, other exported proteins may not directly mediate adhesion.

Since the development of the smallpox vaccine by Jenner in the 18th century, vaccination has been an important armament in the arsenal against infectious microorganisms. Prior to the introduction of antibiotics, vaccination was the major hope for protecting populations against viral or bacterial infection. With the advent of antibiotics in the early 20th century, vaccination against bacterial infections became much less important. However, the recent insurgence of antibiotic-resistant strains of infectious bacteria has resulted in the reestablishment of the importance of anti-bacterial vaccines.

One possibility for an anti-bacterial vaccine is the use of killed or attenuated bacteria. However, there are several disadvantages of whole bacterial vaccines, including the possibility of a reversion of killed or attenuated bacteria to virulence due to incomplete killing or attenuation and the inclusion of toxic components as contaminants.

Another vaccine alternative is to immunize with the bacterial carbohydrate capsule. Presently, vaccines against *Streptococcus pneumoniae* employ conjugates composed of the capsules of the 23 most common serotypes of this bacterium. These vaccines are ineffective in individuals most susceptible to pathological infection—the young, the old, and the immune compromised—because of its inability to elicit a T cell immune response. A recent study has shown that this vaccine is only 50% protective for these individuals [Shapiro et al., *N. Engl. J. Med.* 325:1453-60 (1991)].

An alternative to whole bacterial vaccines are acellular vaccines or subunit vaccines in which the antigen includes a bacterial surface protein. These vaccines could potentially overcome the deficiencies of whole bacterial or capsule-based vaccines.

Moreover, given the importance of exported proteins to bacterial virulence, these proteins are an important target for therapeutic intervention. Of particular importance are proteins that represent a common antigen of all strains of a particular species of bacteria for use in a vaccine that would protect against all strains of the bacteria. However, to date only a small number of exported proteins of Gram positive bacteria have been identified, and none of these represent a common antigen for a particular species of bacteria.

Recently, apparent fusion proteins containing PhoA were exported in species of Gram positive and Gram negative bacteria (Pearce and Masure, 1992, *Abstr. Gen. Meet. Am. Soc. Microbiol.* 92:127,abstract D-188). This abstract reports insertion of pneumococcal DNA upstream from the *E. coli* phoA gene lacking its signal sequence and promoter in a shuttle vector capable of expression in both *E. coli* and *S. pneumoniae*, and suggests that similar pathways for the translocation of exported proteins across the plasma membranes must be found for both species of bacteria.

In previous studies, use of random translational gene fusions (PhoA mutagenesis) to identify and alter exported proteins in *Streptococcus pneumoniae* provided insight into putative exported proteins [Pearce et al., *Mol. Microbiol.*, 9:1037 (1993); International Patent Publication No. WO 95/06732, published Mar. 9, 1995; U.S. patent application Ser. No. 08/116,541, filed Sep. 1, 1993; U.S. patent application Ser. No. 08/245,511, filed May 18, 1994]. Coupling this gene fusion technology to bioactivity assays for pneumococcal adherence, the primary goal was to genetically identify and characterize immunogenic adhesion virulence determinants to eucaryotic cells that define the bacteria-host relationship and thus serve as vaccine candidates. Over 25 loci that effect adherence have been identified as determinants of virulence.

In addition, the molecular mechanism of pathogenesis caused by pneumococcus are beginning to be defined [Cundell, et al., *Infect. Immun.* 63:2493-2498 (1995); Wizemann, et al., *Proc. Natl. Acad. Sci. USA* (1996); Cundell, et al., *J. Cell Biol.* S18A:45 (1994); Spellerberg, et al., *Mol. Microb.* (1996)]. The results of these efforts shows that many bacterial components participate in a complex coordinated process to cause disease. However, it is also apparent that this strategy has produced only a few potential vaccine candidates.

Of note in the search for exported pneumococcal proteins that might be attractive targets for a vaccine is pneumococcal surface protein A (PspA) [see Yother et al., *J. Bacteriol.*, 174:610 (1992)]. PspA has been reported to be a candidate for a *S. pneumoniae* vaccine as it has been found in all pneumococci to date; the purified protein can be used to elicit protective immunity in mice; and antibodies against the protein confer passive immunity in mice [Talkington et al., *Microb. Pathog*. 13:343-355 (1992)]. However, PspA demonstrates antigenic variability between strains in the N-terminal half of the protein, which contains the immunogenic and protection eliciting epitopes (Yother et al., supra). This protein does not represent a common antigen for all strains of *S. pneumoniae*, and therefore is not an optimal vaccine candidate.

Pneumococcal Choline Binding Proteins

Previous studies have shown that PspA, as well as one other surface exposed protein, LytA, the autolytic amidase, bind to teichoic acid (TA), an integral part of the cell wall of *Streptococcus pneumoniae* in a choline-dependent manner. TA contains a unique terminal phosphorylcholine moiety. PspA, a protein having a molecular weight of 84 kDa, and which is highly variable, is released from the cell surface with high choline concentration. Lyt, or autolysin, is a 36 kDa protein, which lyses the pneumococcal cell wall (self lysis), but is not released from the cell by growth in high concentrations of choline, by washing in 10% choline, or by growth in ethanolamine. Reports on choline binding proteins include those by Sanchez-Puelles et al *Gene* 89:69-75 (1990), Briese and Hakenback *Eur. J. Biochem*. 146:417-427, Yother and White *J. of Bacteriol*. 176:2976-2985, Sanchez-Beato et al *J. of Bacteriol*. 177:1098-1103, and Wren *Micro. Review Mol. Microbiol*. 5:797-803 (1991), which are hereby incorporated by reference in their entirety.

A variety of covalent and non-covalent mechanisms of attachment have been described for proteins decorating the surfaces of gram positive bacteria. Some streptococci and *Clostridium sp.* have phosphorylcholine as a unique component of the cell wall. This molecule is the terminal constituent of the teichoic acid (C polysaccharide) and lipoteichoic acid (LTA) attached to the cell wall and plasma membrane of these bacteria. A family of choline binding proteins (CPBs) have also been described which serve a variety of cellular functions. These proteins consist of an N-terminal activity domain and a repeated C-terminal signature choline binding domain that anchors these molecules to the surface of the bacteria. This motif has been identified in the C-terminal regions of a secreted glycoprotein from *Clostridium acetobutylicum* NCIB 88052 [Sanchez-Beato, et al., *J. Bacteriol*. 177:1098-1103 (1995)], toxins A and B from *Clostridium difficile* [Von Eichel-Streiber and Sauerborn, *Gene* 96:107-13 (1990); Von Eichel-Streiber et al., *J. Bacteriol*. 174:6707-6710(1992)], a glucan-binding protein from *Streptococcus mutans*, several glycosyltransferases from *Streptococcus downei* and *S. mutans*, the murein hydrolase (LytA) from pneumococcus and pneumococcal lytic phage [Ronda et al., *Eur. J. Biochem*. 164:621-4,(1987); Diaz et al., *J. Bacteriol*. 174:5516-25 (1992); Romero et al., *Microb. Lett*. 108:87-92 (1993); Yother and White, *J. Bacteriol*. 176:2976-85 (1994)], and a surface antigen (PspA) also from pneumococcus.

Pathology of Pneumococcal Adherence

*S. pneumoniae* is a gram positive bacteria which is a major cause of invasive infections such as sepsis and meningitis [Tuomanen et al., *N. Engl. J. Med*. 322:1280-1284(1995)]. The pneumococcus colonizes the nasopharyngeal epithelium and then penetrates the epithelium of the lung or nasopharynx in order to reach the vascular compartment. Such translocation would involve, of necessity, passage from an epithelial site through the underlying basement membrane/extracellular matrix and across endothelia. Pneumococci have been demonstrated to adhere to epithelia, endothelia and basement membrane in vitro and in vivo [Plotkowski et al., *Am. Rev. Respir. Dis*., 134 (1986); Cundell and Tuomanen, *Microb Path*., 17:361-374 (1994); Cundel et al., *Nature*, 377:435-438 (1995); van der Flier et al., *Infect. Immun*., 63:4317-4322 (1995).

Fibronectin is a mammalian glycoprotein present as a soluble dimer (molecular weight of 550 kDa) in body fluids such as plasma (200-700 mg/ml), cerebrospinal fluid and amniotic fluid and as a less soluble multimer in the extracellular matrix and basement membrane [Ruoslahti, *Ann. Rev. Biochem*., 57:375-413 (1988)]. Fibronectin has specific binding sites for a number of proteins including collagen, integrins, and two binding sites for heparin. Many microorganisms bind fibronectin, including oral streptococci and some gram negative bacteria [Westerlund and Korhonen, *Mol. Microbiol*., 9:687-694 (1993)]. These diverse pathogens all target the Type 1 repeats of the N-terminal heparin binding domain of fibronectin. The cognate fibronectin binding proteins demonstrate a similar amino acid sequence motif consistent with binding to the same target within fibronectin [Westerlund and Korhonen, 1993, supra]. In contrast to this pattern, *Streptococcus pneumoniae* was found to adhere avidly to immobilized fibronectin at the carboxyterminal heparin binding domain [van der Flier et al., *Infect. Immun*. 63:4317-4322, (1995)]. This domain of fibronection has a number of biological activities. It contains the major proteoglycan binding domain (Hep II) and also supports binding of the leukocyte integrin VLA-4 at two regions in the type III connecting segment (IIICS) [Wayner et al., *Cell. Biol*., 109: 1321-1330 (1989; Guan and Hynes, *Cell*, 60:53-61 (1990); Mould et al., *J. Biol. Chem*., 266:3579-3585 (1991)]. The VLA-4 binding domain is distinct from that containing the RGD motif for binding fibronectin by VLA-5 [Pierschbacher et al., *Cell*, 26:259-267 (1981).

The IIICS segment is subject to alternative splicing and is absent in some soluble forms of fibronectin [Guan and Hynes, 1990, supra].

VLA-4, $\alpha 4\beta 1$ (CD49d/CD29), is an integrin present on lymphocytes, monocytes, muscle cells and melanoma cells which mediates binding to VCAM-1 on endothelial cells and myoblasts and to the IIICS domain of fibronectin in the subendothelial matrix [Osborn et al., *Cell*, 59:1203-1211 (1989); Mould et al., *J. Biol. Chem*. 254:4020-4024 (1990); Shimizu et al., *Immunological Reviews*, 114:109-143 (1990); Rosen et al., *Cell*, 69:1107-1119 (1992)]. These interactions are important during infiltration of mononuclear cells to sites of inflammation, metastasis of melanoma cells and in myogenesis [McCarthy et al., *J. Cell. Biol*. 102:179-188 (1986); Osborn et al., 1898, supra; Shimuzu et al., 1990, supra; Rosen et al., 1992, supra]. VLA-4 targets a 25 amino acid region (CS1) with the IIICS domain of fibronectin, an interaction which can be blocked by the tripeptide Leu-Asp-Val [Guan and Hynes, 1990, supra; Komoriya et al., *J. Biol. Chem*. 266:15075-15079 (1991); Mould et al., 1991, supra]. An homologous motif IDSP is present in the VLA4 binding sites in VCAM-1 domains I and IV [Clements et al., *J. Cell. Sci*., 107:2127-2135 (1994)]. The binding sites on VLA-4 for VCAM-1 and fibronection have been suggested to be distinct but overlapping [Elices et al., *Cell*, 50:577-584 (1990); Pulido et al., *J. Biol. Chem*., 266:10241-10245 (1991); Vonderheide and Springer, *J. Exp. Med*., 175:1433-1442 (1992); Makarem, *J. Biol. Chem*. 269:4005-4011 (1994)]. The ability of pneumococci to target the HepII region of fibronectin raised the possibility that these bacteria recognized the region common between HepII and VCAM-1 and that the binding was mediated by a bacterial version of VLA-4. Such interactions could promote passage of pneumococci across the basement membrane. The importance of VLA-4-VCAM-1 interactions for leukocyte trafficking to brain also suggested a role for pneumococcal transmigration into the central nervous system in meningitis.

Therefore, in view of the aforementioned deficiencies attendant with prior art methods of vaccinating against bacterial pathogens, it should be apparent that there still exists a need in the art for identifying protein antigens suitable for use as subunit vaccines, and for use in inducing antibodies suitable for use in passive immunization.

The citation of any reference herein should not be construed as an admission that such reference is available as prior art to the invention.

SUMMARY OF THE INVENTION

In accordance with the present invention, bacterial surface antigens are provided which are suitable for use in immunizing animals against bacterial infection. More particularly, novel choline binding proteins from streptococci, preferably pneumococci, are provided.

In a further embodiment, a method is provided for isolating and identifying choline binding proteins, and the genes encoding them.

In its broadest aspect, the present invention extends to streptococcal surface antigens, generally referred to herein as choline binding proteins, having the following characteristics:

a) binding to choline; and
b) eluting from a choline affinity chromatographic column in the presence of 10%, preferably at least 10%, choline in Dubelcco's phosphate buffered saline (DPBS);

with the proviso that the bacterial surface antigen of the present invention is not PspA or autolysin (LytA). In a preferred aspect, the choline binding protein of the invention has one or more of a characteristic selected from the group consisting of:

c) inhibiting adherence of the bacteria to host cells;
d) being reactive with sera from patients infected or recovering from infection with the bacteria;
e) being reactive with rabbit antisera generated against purified choline binding proteins isolated from a choline affinity column by elution in 10% choline, DPBS; and
f) labeled by fluorescein isothiocyanate (FITC) without requiring bacterial lysis (i.e., in intact bacteria).

In a specific example, the bacterial surface antigen is isolated from pneumococcus.

In a still further aspect, the present invention extends to vaccines based on the choline binding proteins.

In a particular embodiment, the present invention relates to all members of the herein disclosed family of bacterial surface antigens which bind choline, with the proviso that this group does not include PspA or LytA.

In a preferred embodiment, the invention provides a choline binding protein with a high degree of sequence similarity to enolase, particularly *B. subtilis* enolase.

The present invention also relates to an isolated nucleic acids, such as recombinant DNA molecule or cloned gene, or a degenerate variant thereof, which encodes a bacterial choline binding protein (CBP) of the invention. Preferably, the nucleic acid molecule, in particular a recombinant DNA molecule or cloned gene, encoding the CBP has a nucleotide sequence or is complementary to a DNA sequence or fragment thereof which codes on expression for an amino acid having a sequence as follows:

```
CBP112                                  (SEQ ID NO: 1)
XENEGSTQAATSSNMAKTEHRKAAKQVVDE

CBP90                                   (SEQ ID NO: 2)
AREFSLEKTR

CBP84                                   (SEQ ID NO: 3)
XREFSLEKTRNIGIMAHVDAGKT

CBP80                                   (SEQ ID NO: 4)
XKXXWQXKQYLKEDGSQAANEXVFDTA

CBP78                                   (SEQ ID NO: 5)
QKIIGIDLGTTNSAVAVLEGTESKIIANPE

CBP70                                   (SEQ ID NO: 6)
XXXEVAKXSQDTTTAS

CBP60                                   (SEQ ID NO: 7)
XNERVKIVATLGPAVEGRG

CBP50                                   (SEQ ID NO: 8)
XIIXXVYAREVLDSRGNP

CBP112-Int1                             (SEQ ID NO: 9)
EDRRNYHPTNTYK

CBP112-Int2                             (SEQ ID NO: 10)
XDDQQAEEDYA
```

Almost Full Length CBP50 (SEQ ID NO:19)
Partial CBP112 (SEQ ID NO:21)

In a specific embodiment a nucleic acid of the invention, encodes at least a portion (an internal fragment) of the choline binding protein CBP50, preferably having a nucleotide sequence depicted in SEQ ID NO:18; or a portion of the 5' region of the gene encoding binding protein CBP112, preferably having a nucleotide sequence depicted in SEQ ID NO:20.

The DNA sequences encoding the CBPs of the present invention, or portions thereof, may be prepared as probes to screen for complementary sequences and genomic clones in the same or alternate species. The present invention extends to probes so prepared that may be provided for screening. For example, the probes may be prepared with a variety of known vectors, such as the phage λ vector. Such probes are useful for diagnosis, e.g., to confirm a species or strain of Gram positive bacterial infection, as well as for cloning cDNA or genes encoding CBPs.

The present invention also includes CBPs having the activities noted herein, and that display the amino acid sequences set forth and described above and selected from SEQ ID NOS: 1, 2, 3, 4, 5, 6, 7, 8, 9, 10, 19, and 21.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present CBP(s), and more particularly, the DNA sequences or fragments thereof determined from the sequences set forth above and in SEQ ID NOS:18 and 20.

According to other preferred features of certain preferred embodiments of the present invention, a recombinant expression system is provided to produce biologically active CBPs or immunologically reactive portions thereof.

The concept of the bacterial surface antigens contemplates that specific factors exist for correspondingly specific binding proteins, such as CBPs and the like, as described earlier. Accordingly, the exact structure of each CBP will understandably vary so as to achieve this choline-binding and activity specificity. It is this specificity and the direct involvement of the CBP in the adherence of the bacteria, that offers the promise of a broad spectrum of diagnostic and therapeutic utilities.

The present invention naturally contemplates several means for preparation of the CBPs, including as illustrated herein known recombinant techniques, and the invention is accordingly intended to cover such synthetic preparations within its scope. The isolation of the DNA and amino acid sequences disclosed herein facilitates the reproduction of the CBPs by such recombinant techniques, and accordingly, the invention extends to expression vectors prepared from the disclosed DNA sequences for expression in host systems by recombinant DNA techniques, and to the resulting transformed hosts.

A particular advantage of the present invention is that it provides for preparation of sufficient quantities of CBPs for commercialization of anti-CBP vaccines. A further advantage is that the invention provides for preparation of multi-component vaccines containing two or more CBPs, thus broadening and increasing the potential effectiveness of the vaccine. In its primary aspect, the invention contemplates utilizing the CBPs of the invention, either separately or in combinations of two or more, in vaccines for protection against pneumococcal infection. Preferably, a vaccine comprising two or more CBPs further comprises PspA, LytA, or both. According to the invention, CBPs may be prepared recombinantly. Alternatively, CBPs may be obtained from bacterial cultures, e.g., using the purification methods described and exemplified herein. In a specific embodiment, a mixture of CBPs from pneumococcus are obtained, e.g., by choline affinity chromatography, and are used directly without further purification to immunize an animal and elicit protective antibodies. Such a mixture of choline affinity purified proteins may be obtained from bacteria that express PspA or that lack PspA expression (i.e., PspA$^-$ bacteria as exemplified herein).

In another aspect, the genes (e.g., cDNA) encoding one or more CBPs of the invention are engineered in a transgenic vector for expression in a mammalia host in vitro, as a nucleic acid-based vaccine.

In yet another embodiment, the CBPs of the invention are used to generate antibodies for passive immunization, diagnostics, or screening. In a specific example, infra, passive immunization prevents death from pneumococcal infection in a murine model.

The diagnostic utility of the present invention extends to the use of binding partners, notably antibodies, to the present CBPs in assays to screen for bacterial infection.

Antibodies against the CBP(s) include naturally raised and recombinantly prepared antibodies. Such antibodies could be used to screen expression libraries to obtain the gene or genes that encode the CBP(s). These may include both polyclonal and monoclonal antibodies prepared by known genetic techniques, as well as bi-specific (chimeric) antibodies, and antibodies including other functionalities suiting them for additional diagnostic use conjunctive with their capability of modulating bacterial adherence.

Thus, the CBPs, their analogs and/or analogs, and antibodies that may be raised thereto, are capable of use in connection with various diagnostic techniques, including immunoassays, such as a radioimmunoassay, using for example, an antibody to the CBP that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{86}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the bacterial infection, or to identify drugs or other agents that may mimic or block such infection. The system or test kit may comprise a labeled component prepared by one of the radioactive and/or enzymatic techniques discussed herein, coupling a label to the CBPs, their agonists and/or antagonists, and one or more additional immunochemical reagents, at least one of which is a free or immobilized ligand, capable either of binding with the labeled component, its binding partner, one of the components to be determined or their binding partner(s).

In particular, the proteins of CBPs whose sequences are presented in SEQ ID, NOS:1-10, 19 and 20 herein, their antibodies, agonists, antagonists, or active fragments thereof, could be prepared in pharmaceutical formulations for administration in instances wherein antibiotic therapy is appropriate, such as to treat or prevent bacterial infection. Such free proteins could compete with bacterial CBP function, thus interfering with bacterial pathological activity such as adhesion.

In a preferred aspect, the invention provides a method and associated compositions for treating infection with a bacterium that expresses a streptococcal choline binding protein comprising administering pulmonarily an adhesion inhibitory agent selected from the group consisting of a choline binding protein having the following characteristics:

choline-binding activity; and elution from a chromatographic column in the presence of 10% choline;

with the proviso that the streptococcal choline binding protein is not PspA or autolysin (LytA), an antibody to the choline binding protein, an enolase, a hindered cationic small molecule, the peptide WQPPRARI (SEQ ID NO:11), and an antibody specific for an epitope having the amino acid sequence WQPPRARI (SEQ ID NO:11). Preferably, the hindered cationic small molecule is selected from the group consisting of lysine, choline, and arginine. In a further embodiment, the adhesion inhibitory agent is administered with another drug, such as an antibiotic, a steroid, a non-steroidal anti-inflammatory drug, etc.

Accordingly, it is a principal object of the present invention to provide a CBP and its subunits in purified form.

It is a further object of the present invention to provide antibodies to the CBP and its subunits, and methods for their preparation, including recombinant means.

It is a further object of the present invention to provide a method for detecting the presence of the CBP and its subunits in mammals in which invasive, spontaneous, or idiopathic pathological states are suspected to be present.

It is a still further object of the present invention to provide method for the treatment of mammals to control the amount or activity of the bacteria, the CBP or subunits thereof, so as to alter the adverse consequences of such presence or activity, or where beneficial, to enhance such activity.

It is a still further object of the present invention to provide a method for the treatment of mammals to control the amount or activity of the bacteria or its subunits, so as to treat or avert the adverse consequences of invasive, spontaneous, or idiopathic pathological states.

It is a still further object of the present invention to provide pharmaceutical compositions for use in therapeutic methods which comprise or are based upon the CBP, its subunits, or their binding partner(s).

Other objects and advantages will become apparent to those skilled in the art from a review of the ensuing description which proceeds with reference to the following illustrative drawings and Detailed Description of the Invention.

BRIEF DESCRIPTION OF THE DRAWINGS

FIG. 10. Comparison of amino terminal sequence of 50 kDa protein with B. subtilis enolase.

FIG. 14. DNA Sequence comparison of DNA for the 50 kDa protein (SEQ ID NO:14) and B. subtilis enolase (SEQ ID NO:15). The sequences were 74% identical.

FIG. 15. Deduced amino acid sequence comparison for the 50 kDa protein (SEQ ID NO:16) and B. subtilis enolase (SEQ ID NO:17). These sequences were 72% identical, with 85% positives.

DETAILED DESCRIPTION

Figure 1:
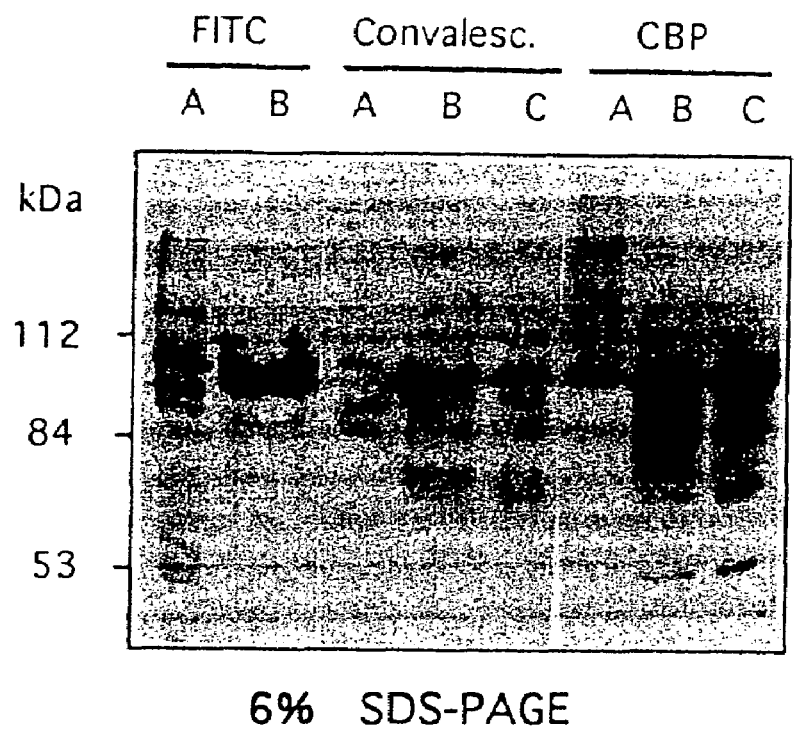
FIG. 1. Western blot of a 6% SDS-PAGE on which bacterial surface proteins were separated. Lane A represents FITC-labelled surface proteins from LM91 (PspA⁻). Lane B represents FITC-labelled surface proteins from LM91 after choline affinity chromatography. Lane C represents LM91 proteins after choline affinity chromatography (CBRO). "FITC" indicates anti-FITC (mouse) antibody was used. "Convalesc." indicates human convalescent (post-pneumococcal infection) antibody was used. "CBP" indicates anti-CBP antibody (rabbit) was used.

As noted above, the present invention is directed to bacterial surface antigens that are suitable for use in immunizing animals against bacterial infection. More particularly, novel choline binding proteins from pneumococci are provided.

These proteins, which are found at the surface of pneumococci, when formulated with an appropriate adjuvant, are used in vaccines for protection against pneumococci, and against other bacteria with cross-reactive choline binding proteins.

As has been previously reported, S. pneumoniae adheres to fibronectin at a site within the carboxy-terminal heparin II binding domain [Flier et al., Infect. Immun. 63:4317 (1995)]. An eight amino acid stretch within the type III # 14 repeat supports adherence. The present invention is based, in part, on the discovery that the pneumococcal adhesin for fibronectin appears to be a choline-binding protein of approximately 50 kDa. This protein has significant homology to the glycolytic enzyme enolase. For example, preincubation of S. pneumoniae with rsVCAM inhibits adherence to whole fibronectin by 96%, and S. pneumoniae adhere directly to rsVCAM with 6% of adherence to whole fibronectin. In addition, pneumococci bind directly to a synthetic peptide, Fn5, based on the Heparin II type III #14 region, having the sequence WQPPRARI (SEQ ID NO:11). Antibody to Fn5 inhibits adherence of S. pneumoniae to whole fibronectin by greater than 70% (1:100). The data exemplified herein show that S. pneumoniae grown in ethanolamine vs. choline results in a greater than 90% decrease in adherence. Preparations of CBP competitively inhibit adherence of S. pneumoniae to fibronectin by 75-90%. Anti-choline antibody inhibits adherence of S. pneumoniae to fibronectin by greater than 95% at dilution of 1:10 to 1:5000. Pretreatment of S. pneumoniae in 10% choline results in greater than 50% decrease in adherence to fibronectin.

In a particular embodiment, the present invention relates to all members of the herein disclosed pneumococcal CBPs, with the proviso that this group does not include Lyt or PspA. In a specific embodiment, a CBP of the invention is a homolog of enolase.

The possibilities both diagnostic and therapeutic that are raised by the existence of the CBP, derive from the fact that the CBP appears to participate in direct and causal protein-protein interaction between the bacteria and its host cell. As suggested earlier and elaborated further on herein, the present invention contemplates pharmaceutical intervention in the binding reaction in which the CBP is implicated, to modulate the activity initiated by the binding of the CBP.

In a further embodiment, a method is provided for isolating and identifying choline binding proteins, and the genes encoding them. More particularly, isolation of the genes encoding choline binding proteins of the invention allows for recombinant production of the proteins, which greatly increases the ability to generate cost-effective vaccines.

The choline binding protein streptococcal surface antigens of the invention have the following characteristics:

a) binding to choline; and
b) eluting from a choline affinity chromatographic column in the presence of 10% choline in Dulbecco's phosphate buffered saline (DPBS);

with the proviso that the streptococcal surface antigen of the present invention is not PspA or autolysin (LytA). In a preferred aspect, the choline binding protein of the invention has one or more of a characteristic selected from the group consisting of:

c) inhibiting adherence of the bacteria to host cells;
d) being reactive with sera from patients infected or recovering from infection with the bacteria;
e) being reactive with rabbit antisera generated against purified choline binding proteins isolated from a choline affinity column by elution in 10% choline, DPBS; and
f) labeled by fluorescein isothiocyanate (FITC) without requiring bacterial lysis (i.e., in intact bacteria).

In a specific example, infra, the streptococcal surface antigen is isolated from pneumococcus by affinity chromatography on a choline agarose column by elution with 10% choline.

In a further embodiment, exemplified herein, a peptide based on the heparin II type III #14 region of fibronectin binds the streptococcal enolase homolog of the invention. In a specific embodiment, the peptide is Fn5 having an amino acid sequence WQPPRARI (SEQ ID NO:11). Whole pneumococci adhere to this peptide prepared synthetically. Thus, the free peptide would be expected to inhibit enolase-mediated adherence to fibronectin in vivo. In addition, an antibody specific for this peptide inhibits pneumococcal adherence to fibronectin. In a specific embodiment, an anti Fn5 antibody inhibits adherence of S. pneumoniae to whole fibronectin by greater than 70%.

The term "bacterial" used herein refers to Gram positive bacteria with choline binding proteins homologous to the proteins exemplified herein. The present invention is more particularly directed to streptococcal CBPs and most particularly to pneumococcal CBPs.

The terms "bacterial (or streptococcal or pneumococcal) surface antigen", "choline binding protein (CBP)" and any variants not specifically listed, may be used herein interchangeably, and as used throughout the present application and claims refer to proteinaceous material including single or multiple proteins, and extends to those proteins having the amino acid sequence data described herein and identified by (SEQ ID NOS:1-10, 19, and 20), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "bacterial (or streptococcal or pneumococcal) surface antigen", and "choline binding protein (CBP)" are intended to include within their scope proteins specifically recited herein as well as all substantially homologous analogs and allelic variations.

The term "enolase" refers to the enzyme 2-phospho-D-glycerate hydrolyase.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. Abbreviations used herein are in keeping with standard polypeptide nomenclature, J. Biol. Chem., 243:3552-59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Purification of CBPs

Teichoic acid (TA), an integral part of the cell wall of Streptococcus pneumoniae contains a unique terminal phosphorylcholine moiety. Choline affinity chromatography or Mono-Q Sepharose, a close relative of choline were used to purify the CBPs. It is important to note that initially these proteins were purified from a capsulated strain of pneumococcus that was genetically altered not to produce PspA, a major CBP. The purification schemes are as follows:

Whole bacteria are incubated with either choline-agarose or Mono-Q Sepharose.

Bacteria are lysed with detergent and unbound material washed with 0.5 M NaCl.

Figure 3:
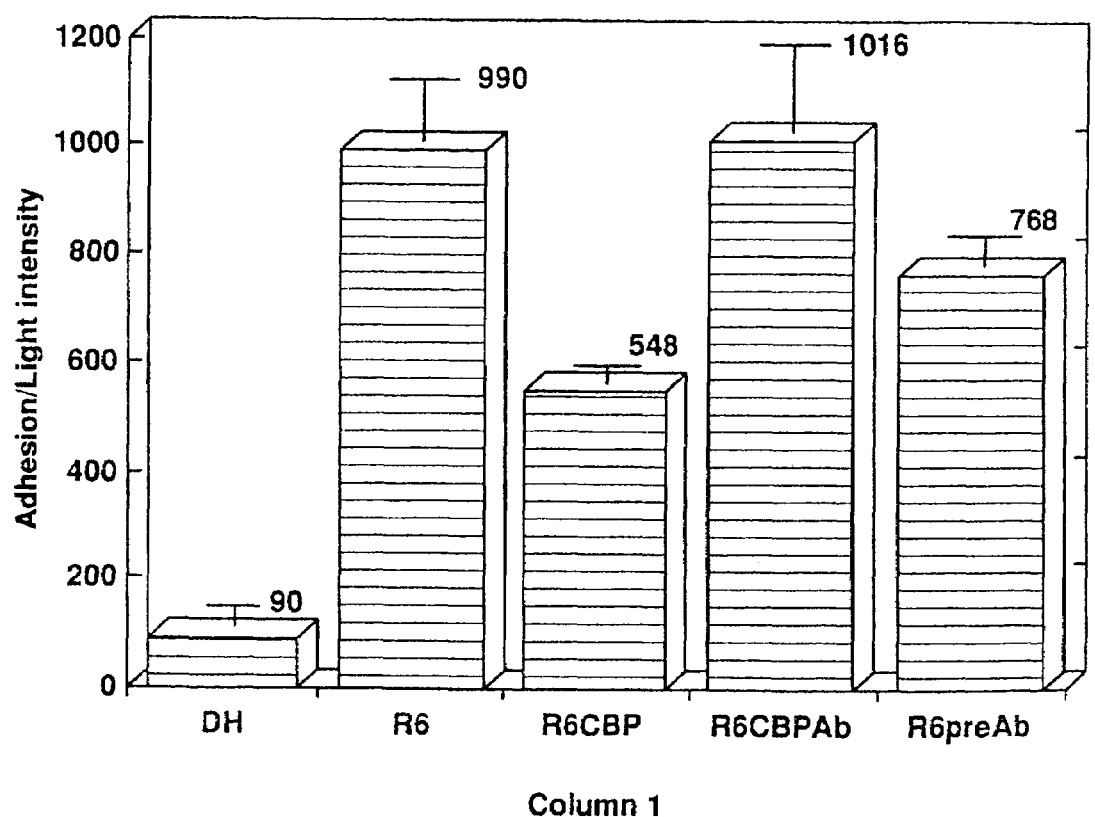
FIG. 3. Adhesion assay of PN R6 to lung cell A549.

CBPs are eluted with either with 0.5 M choline chloride or with a linear choline chloride gradient. The molecular masses of proteins purified by these two methods are summarized in Table 1 (see FIG. 1).

infection. Compared to controls, the CBP fraction blocked pneumococcal adherence by 45% to LC and 89% to EC in a dose dependent manner (FIG. 3). Based on these results it is most likely that the fraction of CBPs contain adhesins involved in the binding of bacteria to eucaryotic target cells. The contribution of each of these CBPs to block the adhesive properties of parental bacteria can be assessed, for example, to block the binding of pneumococcus to epithelial (type II lung cells), endothelial (human umbilical vein endothelial cells) cells, and immobilized glycoconjugates that contain GlcNAcβ1-4Gal, GlcNAcβ1-3Gal, GlcNAc, or other sugars that have been shown to be analogs for eucaryotic receptors.

TABLE 1

Criteria for the identification of choline binding proteins as vaccine candidates from a capsulated PspA deficient strain of pneumococcus*

| Purification Scheme | SDS-PAGE 10% | | Labeling of surface proteins | | Rabbit antisera to whole bacteria | | Human convalescent serum | |
|---|---|---|---|---|---|---|---|---|
| Cell lysate | | | 112 kDa | 90 kDa | 200 kDa | 112 kDa | 200 kDa | 130 kDa |
| (0.5% Triton x 100) | | | 80 kDa | 75 kDa | 90 kDa | 84 kDa | 112 kDa | 90 kDa |
| | | | 60 kDa | 53 kDa | 75 kDa | 53 kDa | 84 kDa | 82 kDa |
| | | | 37 kDa | 30 kDa | 48 kDa | 45 kDa | 80 kDa | 75 kDa |
| | | | 28 kDa | 20 kDa | 37 kDa | 35 kDa | 60 kDa | 53 kDa |
| Mono-Q Anion | | | | | 5% choline gradient: | | | |
| | | | | | 112 kDa | 84 kDa | | |
| | | | | | 53 kDa | 37 kDa | | |
| Choline-Agarose | 200 kDa | 112 kDa | 112 kDa | 95 kDa | 75 kDa | <35 kDa | 112 kDa | |
| (Elution with 0.5 M | 90 kDa | 84 kDa | 80 kDa | 75 kDa | | | 80 kDa | |
| choline chloride) | 82 kDa | 80 kDa | 70 kDa | 37 kDa | | | 75 kDa | |
| | 75 kDa | 60 kDa | | | | | | |
| | 40 kDa | 37 kDa | | | | | | |

*Bold faced characters represent proteins of interest that are potential vaccine candidates.

Purification of CBPs from the choline agarose affinity chromatography is preferred, with at least 9 proteins with molecular masses ranging from 200 to 40 kDa identifiable this way. A band of 37 kDa was also detected and shown to be LytA with antisera specific for this protein. This is a well characterized CBP and thus served as a positive control.

Criteria for Vaccine Candidates

CBPs may be subjected to a variety of tests to determine if they are good vaccine candidates The criteria for vaccine development, and the characteristics of the isolated CBPs are summarized below.

The CBPs must be surface exposed. Whole bacteria may be chemically labeled with FITC (Fluorescein isothiocyanate) and labeled proteins detected with antisera specific for FITC. (Table 1 and FIG. 1). The CBPs 112, 75, and 80, as well as LytA, were effectively labeled with FITC suggesting that these proteins were surface exposed.

Vaccine candidates must be immunogenic therefore candidate CBPs should react with human convalescent sera. The CBPs 112, 75, and 80 gave a strong signal with pooled human antisera obtained from individuals recovering from pneumococcal disease (FIG. 1).

Figure 2:
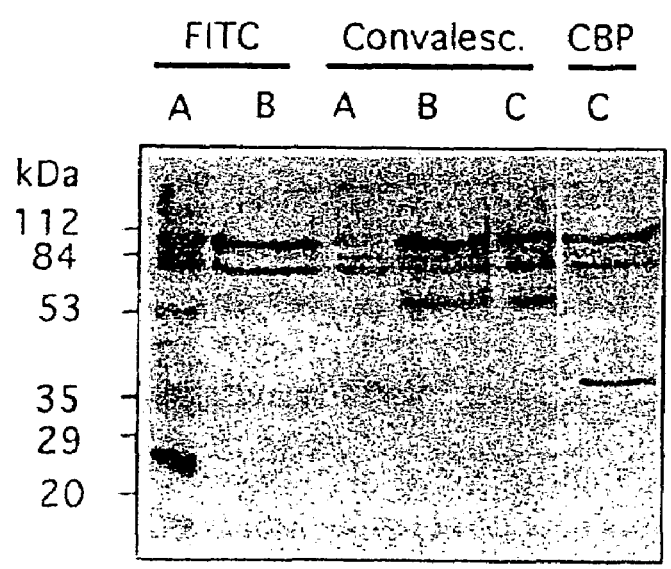
FIG. 2. Western blot of a 10% SDS-PAGE as described in FIG. 1.

Vaccine candidates must be antigenic. The CBPs from choline agarose chromatography were injected into rabbits and sera tested for cross reactivity. Several proteins produced a strong signal. Prominent were CBPs 112, 90, 84 and 70, and 50 (FIGS. 1 and 2).

A good vaccine candidate may block adherence to target cell receptors present within the host at the critical sites of It should be noted that not every CBP may function as an adhesin, similarly, adhesion activity may be a collateral characteristic of CBPs.

A preferred vaccine candidate will elicit a protective immune response without antigenic variability among in clinical serotypes. Antisera (either monoclonal or polyclonal) to each CBP will be generated to determine if the native and the recombinant CBPs are immunogenic. CBP specific antibodies will be used to screen relevant pneumococcal serotypes for antigenic variability.

In a more preferred aspect, antibodies to the CBPs will be tested to confirm that they protect against pneumococcal infection, preferably of various strains or serotypes. For example, passively or actively immunized animals are challenged with pneumococcus in models for bacteremia or colonization, or preferably both.

Other criteria to consider in selection of a preferred CBP as a vaccine candidate include testing CBP defective mutants for attenuation of virulence in animal models for bacteremia or colonization efficacy alone or in combination or coupled to a capsular polysaccharide. For example, preliminary data show that CBP112 is expressed in virulent transparent bacteria, but that expression is diminished in avirulent opaque bacteria.

Genes Encoding CBPs

As stated above, the present invention also relates to a recombinant DNA molecule or cloned gene, or a degenerate variant thereof, which encodes a CBP, or a fragment thereof, that possesses a molecular weight of between about 50 kDa and 112 kDa, preferably which has an amino acid sequence set forth in (SEQ ID NOS:1-10, 19 and 20). In a specific aspect, a nucleic acid molecule, in particular a recombinant DNA molecule or cloned gene, encoding the 50-112 kDa CBP has a nucleotide sequence or is complementary to a DNA sequence shown in (SEQ ID NO:18 or 20).

In accordance with the present invention there may be employed conventional molecular biology, microbiology, and recombinant DNA techniques within the skill of the art. Such techniques are explained fully in the literature. See; e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding CBPs which code for a CBP having the same amino acid sequence as one of SEQ ID NOS:1-5, but which are degenerate to an oligonucleotide rep resented by the purified natural (i.e., native) gene, e.g., by SEQ ID NO:11. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCC |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have a T substituted for U.

Completely degenerate oligonucleotides can be designed based on the amino acid sequence encoding the CBP, taking into account the above degenerates. Likewise, where a codon encoding an amino acid is not known with certainty, e.g., due to degeneracy of the genetic code, inosine may be included at the unknown position.

Mutations can be made in a nucleic acid encoding a CBP such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The present invention extends to the preparation of oligonucleotides that may be used to hybridize with nucleic acids encoding CBPs.

As mentioned above, a DNA sequence encoding a CBP can be prepared synthetically rather than cloned. The DNA sequence can be designed with the appropriate codons for the CBP amino acid sequence. In general, one will select preferred codons for the intended host if th sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223: 1299 (1984); Jay et al., *J. Biol. Chem.*, 259:6311 (1984).

Synthetic DNA sequences allow convenient construction of genes which will express CBP analogs or "muteins". Alternatively, DNA encoding muteins can be made by site-directed mutagenesis of native CBP genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

Recombinant Production of CBPs

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that CBP analogs may be prepared from nucleotide sequences of the protein complex/subunit derived within the scope of the present invention. Analogs, such as fragments, may be produced, for example, by pepsin digestion of CBP or bacterial material. Other analogs, such as muteins, can be produced by standard site-directed mutagenesis of CBP coding sequences. Analogs exhibiting "choline-binding activity" such as small molecules, whether functioning as promoters or inhibitors, may be identified by known in vivo and/or in vitro assays.

Antibodies to CBPs

As noted above, the CBPs of the invention, whether obtained by purification from bacterial sources or recombinantly, can be used to generate antibodies for diagnosis and therapy, as set forth in detail below. Thus, preferred CBPs of the invention are antigenic, and more preferably immunogenic.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting a humoral immune response without a carrier.

An "antibody" for purposes of this invention is any immunoglobulin, including antibodies and fragments thereof, that binds a specific epitope on a CBP. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

According to the invention, CBP(s) produced recombinantly, by chemical synthesis, or purified from the natural bacterial source, and fragments or other derivatives or analogs thereof, including fusion proteins, may be used as an immunogen to generate anti-CBP antibodies. Such antibodies include but are not limited to polyclonal, monoclonal, chimeric, single chain, Fab fragments, and an Fab expression library.

Various procedures known in the art may be used for the production of polyclonal antibodies to CBPs or derivatives or analogs thereof (see, e.g., *Antibodies—A Laboratory Manual*, Harlow and Lane, eds., Cold Spring Harbor Laboratory Press: Cold Spring Harbor, N.Y., 1988). For the production of antibody, various host animals can be immunized by injection with CBP(s), or a derivative (e.g., fragment or fusion protein) thereof, including but not limited to rabbits, mice, rats, sheep, goats, etc. In one embodiment, the CBP or fragment thereof can be conjugated to an immunogenic carrier, e.g., bovine serum albumin (BSA) or keyhole limpet hemocyanin (KLH). Various adjuvants may be used to increase the immunological response, depending on the host species.

For preparation of monoclonal antibodies directed toward the CBP, or fragment, analog, or derivative thereof, any technique that provides for the production of antibody molecules by continuous cell lines in culture may be used (see, e.g., *Antibodies—A Laboratory Manual*, Harlow and Lane, eds., Cold Spring Harbor Laboratory Press: Cold Spring Harbor, N.Y., 1988). These include but are not limited to the hybridoma technique originally developed by Kohler and Milstein (1975, Nature 256:495-497), as well as the trioma technique, the human B-cell hybridoma technique (Kozbbr et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc. pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for a CBP together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce CBP-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for a CBP, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a CBP, one may assay generated hybridomas for a product which binds to a CBP fragment containing such epitope. For selection of an antibody specific to a CBP from a particular strain of Gram positive bacteria, particularly pneumococcus, one can select on the basis of positive binding with CBP expressed by or isolated from cells of that strain of bacteria.

The foregoing antibodies can be used in methods known in the art relating to the localization and activity of the CBP, e.g., for Western blotting, imaging CBP polypeptide in situ, measuring levels thereof in appropriate physiological samples, etc.

In a specific embodiment, antibodies that agonize or antagonize the activity of CBP can be generated. Such antibodies can be tested using the assays described supra for characterizing CBPs.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Vaccination and Passive Immune Therapy

Active immunity against Gram positive bacteria, particularly pneumococcus, can be induced by immunization (vaccination) with an immunogenic amount of an CBP, or an antigenic derivative or fragment thereof, and an adjuvant, wherein the CBP, or antigenic derivative or fragment thereof, is the antigenic component of the vaccine.

The CBP alone or conjugated to a capsule or capsules cannot cause bacterial infection, and the active immunity elicited by vaccination with the protein according to the present invention can result in both an immediate immune response and in immunological memory, and thus provide long-term protection against infection by the bacterium. The CBPs of the present invention, or antigenic fragments thereof, can be prepared in an admixture with an adjuvant to prepare a vaccine. Preferably, the CBP, or derivative or fragment thereof, used as the antigenic component of the vaccine is an adhesin. More preferably, the CBP, or derivative or fragment thereof, used as the antigenic of the vaccine is an antigen common to all or many strains of a species of Gram positive bacteria, or common to closely related species of bacteria. Most preferably, the antigenic component of the vaccine is an adhesin that is a common antigen.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA encoding the antigen into tissues of a subject for expression of the antigen by the cells of the subject's tissue. Such vaccines are termed herein "nucleic acid-based vaccines." Since the CBP gene by definition contains a signal sequence, expression of the gene in cells of the tissue results in secretion of membrane association of the expressed protein. Alternatively, the expression vector can be engineered to contain an autologous signal sequence instead of the CBP signal sequence. For example, a naked DNA vector (see, e.g., Ulmer et al., 1993, Science 259:1745-1749), a DNA vector transporter (e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990), or a viral vector containing the desired CBP gene can be injected into tissue. Suitable viral vectors include tetroviruses that are packaged in cells with amphotropic host range (see Miller, 1990, Human Gene Ther. 1:5-14; Ausubel et al., *Current Protocols in Molecular Biology*, § 9), and attenuated or defective DNA virus, such as but not limited to herpes simplex virus (HSV) (see, e.g., Kaplitt et al., 1991, Molec. Cell. Neurosci. 2:320-330), papillomavirus, Epstein Barr virus (EBV), adenovirus (see, e.g., Stratford-Perricaudet et al., 1992, J. Clin. Invest. 90:626-630), adeno-associated virus (AAV) (see, e.g., Samulski et al., 1987, J. Virol. 61:3096-3101; Samulski et al., 1989, J. Virol. 63:3822-3828), and the like. Defective viruses, which entirely or almost entirely lack viral genes, are preferred. Defective virus is not infective after introduction into a cell.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Either vaccine of the invention, i.e., a vaccines comprising an CBP antigen or antigenic derivative or fragment thereof, or an CBP nucleic acid vaccine, can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen. Since immune cells are continually replicating, they are ideal target for retroviral vector-based nucleic acid vaccines, since retroviruses require replicating cells.

Passive immunity can be conferred to an animal subject suspected of suffering an infection with a Gram positive bacterium, preferably streptococcal, and more preferably pneumoccal, by administering antiserum, polyclonal antibodies, or a neutralizing monoclonal antibody against a choline binding protein of the invention to the patient. Although passive immunity does not confer long term protection, it can be a valuable tool for the treatment of a bacterial infection of a subject who has not been vaccinated. Passive immunity is particularly important for the treatment of antibiotic resistant strains of Gram positive bacteria, since no other therapy may be available. Preferably, the antibodies administered for passive immune therapy are autologous antibodies. For example, if the subject is a human, preferably the antibodies are of human origin or have been "humanized," in order to minimize the possibility of an immune response against the antibodies.

In a specific example, infra, passive immunity completely protects against lethal bacterial infection.

An analogous therapy to passive immunization is administration of an amount of an CBP protein adhesin sufficient to inhibit adhesion of the bacterium to its target cell. The required amount can be determined by one of ordinary skill using standard techniques.

The active or passive vaccines of the invention, or the administration of an adhesin, can be used to protect an animal subject from infection of a Gram positive bacteria, preferably streptococcus, and more preferably, pneumococcus. Thus, a vaccine of the invention can be used in birds, such as chickens, turkeys, and pets; in mammals, preferably a human, although the vaccines of the invention are contemplated for use in other mammalian species, including but not limited to domesticated animals (canine and feline); farm animals (bovine, ovine, equine, caprine, porcine, and the like); rodents; and undomesticated animals.

Diagnosis of a Gram Positive Bacterial Infection

The antibodies of the present invention that can be generated against the CBPs from Gram positive bacteria are valuable reagents for the diagnosis of an infection with a Gram positive microorganism, particularly a pneumococcus. Presently, diagnosis of infection with a Gram positive bacterium is difficult. According to the invention, the presence of Gram positive bacteria in a sample from a subject suspected of having an infection with a Gram positive bacterium can be detected by detecting binding of an antibody to an CBP to bacteria in or from the sample. In one aspect of the invention, the antibody can be specific for a unique strain or a limited number of strains of the bacterium, thus allowing for diagnosis of infection with that particular strain (or strains). Alternatively, the antibody can be specific for many or all strains of a bacterium, thus allowing for diagnosis of infection with that species.

Diagnosis of infection with a Gram positive bacterium can use any immunoassay format known in the art, as desired. Many possible immunoassay formats are described in the section entitled "Antibodies to CBPs." The antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

In specific embodiments, the presence of CBP in or on cells can be ascertained by the usual immunological procedures applicable to such determinations. A number of useful procedures are known. The procedures and their application are all familiar to those skilled in the art and accordingly may be utilized within the scope of the present invention. For example, a "competitive" procedure is described in U.S. Pat. Nos. 3,654,090 and 3,850,752. A "sandwich" procedure, is described in U.S. Pat. Nos. RE 31,006 and 4,016,043. Still other procedures are known such as the "double antibody," or "DASP" procedure.

In each instance, the CBP forms complexes with one or more antibody(ies) or binding partners and one member of the complex is labeled with a detectable label. The fact that a complex has formed and, if desired, the amount thereof, can be determined by known methods applicable to the detection of labels.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The CBP or its binding partner(s) can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or absence of predetermined binding activity or predetermined binding activity capability to suspected target cells. In accordance with the testing techniques discussed above, one class of such kits will contain at least the labeled CBP or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined bacterial binding activity, comprising:

(a) a predetermined amount of at least one labeled immunochemically reactive component obtained by the direct or indirect attachment of the present CBP factor or a specific binding partner thereto, to a detectable label;

(b) other reagents; and (c) directions for use of said kit.

More specifically, the diagnostic test kit may comprise:

(a) a known amount of the CBP as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the CBP to a detectable label;

(b) one or more additional immunochemical reagents of which at least one reagent is a ligand or an immobilized ligand, which ligand is selected from the group consisting of:

(i) a ligand capable of binding with the labeled component (a);
(ii) a ligand capable of binding with a binding partner of the labeled component (a);
(iii) a ligand capable of binding with at least one of the component(s) to be determined; and
(iv) a ligand capable of binding with at least one of the binding partners of at least one of the component(s) to be determined; and (c) directions for the performance of a protocol for the detection and/or determination of one or more components of an immunochemical reaction between the CBP and a specific binding partner thereto.

Alternatively, the nucleic acids and sequences thereof of the invention can be used in the diagnosis of infection with a Gram positive bacterium. For example, the CBP genes or hybridizable fragments thereof can be used for in situ hybridization with a sample from a subject suspected of harboring an infection of Gram positive bacteria. In another embodiment, specific gene segments of a Gram positive bacterium can be identified using PCR amplification with probes based on the CBP genes of the invention. In one aspect of the invention, the hybridization with a probe or with the PCR primers can be performed under stringent conditions, or with a sequence specific for a unique strain or a limited number of strains of the bacterium, or both, thus allowing for diagnosis of infection with that particular strain (or strains). Alternatively, the hybridization can be under less stringent conditions, or the sequence may be homologous in any or all strains of a bacterium, thus allowing for diagnosis of infection with that species.

Therapeutic Compositions and Vaccines Comprising CBPs

As noted above, the present invention provides therapeutic compositions comprising antibodies to CBPs (i.e., passive immune therapy), anti-CBP vaccines (whether comprised of CBPs in an adjuvant, or a nucleic acid vaccine), CBPs to compete with bacterial CBPs for pathogenic activities, such as adherence to host cells, peptides, such as Fn5, or antibodies to Fn5. Preferably, any such composition is a pharmaceutical composition comprising the active component (antibody, vaccine, or CBP) in a pharmaceutically acceptable carrier.

The preparation of therapeutic compositions which contain an active component is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. In the context of the present invention, a deficit in the response of the host is evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

According to the invention, the component or components of a therapeutic composition of the invention may be introduced parenterally, transmucosally, e.g., orally, nasally, pulmonarilly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, Science 249:1527-1533 (1990); Treat et al., in *Liposomes in the Therapy of Infectious Disease and Cancer*, Lopez-Berestein and Fidler (eds.), Liss, N.Y., pp. 353-365 (1989); Lopez-Berestein, ibid., pp. 317-327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, N.Y. (1984); Ranger and Peppas, J. Macrbmol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site of inappropriate immune activation or a tumor.

Other controlled release systems are discussed in the review by Langer (Science 249:1527-1533 (1990)).

A subject in whom administration of an active component as set forth above is an effective therapeutic regiment for a bacterial infection is preferably a human, but can be any animal. Thus, as can be readily appreciated by one of ordinary skill in the art, the methods and pharmaceutical compositions of the present invention are particularly suited to administration to any animal, particularly a mammal and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a bacterial infection, one may administer the present active component in conjunction with one or more pharmaceutical compositions used for treating bacterial infection, including but not limited to (1) antibiotics; (2) soluble carbohydrate inhibitors of bacterial adhesion; (3) other small molecule inhibitors of bacterial adhesion; (4) inhibitors of bacterial metabolism, transport, or transformation; (5) stimulators of bacterial lysis, or (6) anti-bacterial antibodies or vaccines directed at other bacterial antigens. Other potential active components include anti-inflammatory agents, such as steroids and non-steroidal anti-inflammatory drugs. Administration may be simultaneous (for example, administration of a mixture of the present active component and an antibiotic), or may be in serriatim.

Accordingly, in specific embodiment, the therapeutic compositions may further include an effective amount of the active component, and one or more of the following active ingredients: an antibiotic, a steroid, etc. Exemplary formulations are given below:

Formulations

| Ingredient | mg/ml |
|---|---|
| Intravenous Formulation I | |
| cefotaxime | 250.0 |
| CBP | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| CBP | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| CBP | 10.0 |
| sodium bisulfite USP | 3.2 |
| disodium edetate USP | 0.1 |
| water for injection q.s.a.d. | 1.0 ml |
| Intravenous Formulation IV | |
| CBP | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| CBP antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "µg" mean microgram, "mg" means milligram, "ul" or "µl" mean microliter, "ml" means milliliter, "l" means liter.

Thus, in a specific instance where it is desired to reduce or inhibit the infection resulting from CBP-mediated binding of bacteria to a host cell, CBP or an antibody thereto, or a ligand thereof or an antibody to that ligand, such as Fn5, could be introduced to block the interaction of CBP present on bacteria with the host cell.

As discussed earlier, the CBPs or antibodies thereto may be prepared in pharmaceutical compositions, with a suitable carrier and at a strength effective for administration by various means to a patient experiencing an adverse medical condition associated with specific bacterial infection for the treatment thereof. A variety of administrative techniques may be utilized, among them parenteral techniques such as subcutaneous, intravenous and intraperitoneal injections, catheterizations and the like. Average quantities of the CBPs or their subunits may vary and in particular should be based upon the recommendations and prescription of a qualified physician or veterinarian.

Pulmonary Delivery

Also contemplated herein is pulmonary delivery of the present adhesion inhibitory agent (or derivatives thereof), of the invention, selected from the group consisting of a choline binding protein, an antibody to a choline binding protein, an enolase, hindered cationic small molecules (such as lysine, choline, arginine, etc.), the peptide WQPPRARI (SEQ ID NO:11), and antibody specific for an epitope having the amino acid sequence WQPPRARI (SEQ ID NO:11). The adhesion inhibitory agent (or derivative) is delivered to the lungs of a mammal, where it can interfere with bacterial, i.e., streptococcal, and preferably pneumococcal binding to host cells. In a specific embodiment, such an adhesion inhibitory agent inhibits binding of the streptococcal enolase to fibronectin. Other reports of preparation of proteins for pulmonary delivery are found in the art [Adjei et al. *Pharmaceutical Research*, 7:565-569 (1990); Adjei et al., *International Journal of Pharmaceutics*, 63:135-144 (1990) (leuprolide acetate); Braquet et al., *Journal of Cardiovascular Pharmacology*, 13(suppl. 5):143-146 (1989) (endothelin-1); Hubbard et al., *Annals of Internal Medicine*, Vol. III, pp. 206-212 (1989) (α1-antitrypsin); Smith et al., *J. Clin. Invest.* 84:1145-1146 (1989) (α-1-proteinase); Oswein et al., "Aerosolization of Proteins", *Proceedings of Symposium on Respiratory Drug Delivery II*, Keystone, Colo., March, (1990) (recombinant human growth hormone); Debs et al., *J. Immunol.* 140:3482-3488 (1988) (interferon-γ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of adhesion inhibitory agent (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified adhesion inhibitory agent may also be prepared in different formulations depending on the type of chemical modification or the type of device employed.

Formulations suitable for use with a nebulizer, either jet or ultrasonic, will typically comprise adhesion inhibitory agent (or derivative) dissolved in water at a concentration of about 0.1 to 25 mg of biologically active adhesion inhibitory agent per ml of solution. The formulation may also include a buffer and a simple sugar (e.g., for adhesion inhibitory agent stabilization and regulation of osmotic pressure). The nebulizer formulation may also contain a surfactant, to reduce or prevent surface induced aggregation of the adhesion inhibitory agent caused by atomization of the solution in forming the aerosol.

Formulations for use with a metered-dose inhaler device will generally comprise a finely divided powder containing the adhesion inhibitory agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain adhesion inhibitory agent and a dispersing agent in a physiologically acceptable diluent. The dry powder aerosol formulations of the present invention consist of a finely divided solid form of adhesion inhibitory agent and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art.

In a particular embodiment, the mass median dynamic diameter will be 5 micrometers or less in order to ensure that the drug particles reach the lung alveoli [Wearley, L. L., *Crit. Rev. in Ther. Drug Carrier Systems* 8:333 (1991)].

Systems of aerosol delivery, such as the pressurized metered dose inhaler and the dry powder inhaler are disclosed in Newman, S. P., *Aerosols and the Lung*, Clarke, S. W. and Davia, D. editors, pp. 197-22 and can be used in connection with the present invention.

In a further embodiment, as discussed in detail infra, an aerosol formulation of the present invention can include other therapeutically or pharmacologically active ingredients in addition to adhesion inhibitory agent, such as but not limited to an antibiotic, a steroid, a non-steroidal anti-inflammatory drug, etc.

Liquid Aerosol Formulations. The present invention provides aerosol formulations and dosage forms for use in treating subjects suffering from bacterial, e.g., streptococcal, in particularly pneumococcal, infection. In general such dosage forms contain adhesion inhibitory agent in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0-8.0 range, or water.

The liquid aerosol formulation of the present invention may include, as optional ingredients, pharmaceutically acceptable carriers, diluents, solubilizing or emulsifying agents, surfactants and excipients.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising adhesion inhibitory agent and another therapeutically effective drug, such as an antibiotic, a steroid, a non-steroidal anti-inflammatory drug, etc.

Aerosol Dry Powder Formulations. It is also contemplated that the present aerosol formulation can be prepared as a dry powder formulation comprising a finely divided powder form of adhesion inhibitory agent and a dispersant.

Formulations for dispensing from a powder inhaler device will comprise a finely divided dry powder containing adhesion inhibitory agent (or derivative) and may also include a bulking agent, such as lactose, sorbitol, sucrose, or mannitol in amounts which facilitate dispersal of the powder from the device, e.g., 50 to 90% by weight of the formulation. The adhesion inhibitory agent (or derivative) should most advantageously be prepared in particulate form with an average particle size of less than 10 mm (or microns), most preferably 0.5 to 5 mm, for most effective delivery to the distal lung.

In another embodiment, the dry powder formulation can comprise a finely divided dry powder containing adhesion inhibitory agent, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising adhesion inhibitory agent and another therapeutically effective drug, such as an antibiotic, a steroid, a non-steroidal anti-inflammatory drug, etc.

Identification of Small Molecule Antagonists of CBPs

Identification and isolation of a gene encoding a choline binding protein of the invention provides for expression of the protein in quantities greater than can be isolated from natural sources, or in indicator cells that are specially engineered to indicate the activity of a CBP expressed after transfection or transformation of the cells. According, in addition to rational design of agonists and antagonists based on the structure of a choline binding protein, the present invention contemplates an alternative method for identifying specific ligands of a choline binding-protein using various screening assays known in the art. Examples of small molecule antagonists of CBPs include lysine, choline, the pentapeptide having SEQ ID NO:11; it is likely that analogs of these types of molecules, such as arginine, will also inhibit bacterial adhesion to host tissue, particularly fibronectin. Thus, the present invention generally provides a small molecule CBP binding antagonist, which is a hindered cationic molecule, preferably a hindered amine.

Any screening technique known in the art can be used to screen for choline binding protein agonists or antagonists. The present invention contemplates screens for small molecule ligands or ligand analogs and mimics, as well as screens for natural ligands that bind to and agonize or antagonize activities of choline binding protein in vivo, particularly adhesion of bacteria to host cells or tissues mediated by the choline binding protein.

Knowledge of the primary sequence of the CBP, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, Science 249:386-390; Cwirla, et al., 1990, Proc. Natl. Acad. Sci., 87:6378-6382; Devlin et al., 1990, Science, 249:404-406), very large libraries can be constructed ($10^6$-$10^8$ chemical entities). A second approach uses primarily chemical methods, of which the Geysen method (Geysen et al., 1986, Molecular Immunology 23:709-715; Geysen et al. 1987, J. Immunologic Method 102:259-274) and the recent method of Fodor et al. (1991, Science 251, 767-773) are examples. Furka et al. (1988, 14th International Congress of Biochemistry, Volume 5, Abstract FR:013; Furka, 1991, Int. J. Peptide Protein Res. 37:487493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., 1993, "Generation and screening of an oligonucleotide encoded synthetic peptide library," Proc. Natl. Acad. Sci. USA 90:10700-4; Ohlmeyer et al., 1993, Proc. Natl. Acad. Sci. USA 90:10922-10926; Lam et al., International Patent Publication No. WO 92/00252; Kocis et al., International Patent Publication No. WO 9428028, each of which is incorporated herein by reference in its entirety), and the like can be used to screen for choline binding protein ligands according to the present invention.

The screening can be performed with recombinant cells that express the choline binding protein, or alternatively, using purified protein, e.g., produced recombinantly, as described above. For example, the ability of labeled, soluble or solubilized choline binding protein that includes the ligand-binding portion of the molecule, to bind ligand can be used to screen libraries, as described in the foregoing references.

The following examples are presented in order to more fully illustrate the preferred embodiments of the invention. They should in no way be construed, however, as limiting the broad scope of the invention.

EXAMPLES

Preliminary Considerations

The present invention identifies a family of CBPs which are surface exposed proteins and serve as adhesins critical for the binding of pneumococcus to eukaryotic cells found at the sites of infection. The invention also identifies and characterizes a novel CBP, CbpA, as an adhesin and a determinant of virulence. Furthermore, the present invention demonstrates that these proteins are immunogenic and thus may also function as protective antigens.

Using choline bound to agarose beads, a family of at least 12 bacterial choline binding proteins (CBPs), including LytA, was purified from a serotype II, PspA⁻ strain of pneumococcus. Labeling of whole bacteria with fluorescein isothiocyanate (FITC) suggested that four of these CBPs were surface-exposed while human convalescent sera cross-reacted with five of the CBPs. It was previously shown that pneumococcus binds to type II lung cells (LC) and endothelial cells (EC) of the peripheral vasculature. Compared to controls, the CBP fraction blocked pneumococcal adherence by 45% to LC and 89% to EC in a dose-dependent manner. The CBP fraction was used to immunize rabbits, and polyclonal antibodies were used for passive immunization studies. N-terminal and internal amino acid sequence obtained from three of the CBPs showed no similarity to any known protein sequences. Moreover, the predominant member of this family of proteins, CbpA, is a 112 kDa surface exposed protein that reacted with human convalescent sera. Sequence analysis of the corresponding gene showed a unique N-terminal sequence and six C-terminal choline binding domains in the C-terminal region.

Example 1

Identification of Pneumococcal Choline Binding Proteins

Materials and Methods

Strains. Bacterial strains used included (1) R6, an unencapsulated bacterial strain derived from D39 (type 2), unencapsulated, (2) AII encapsulated, (3) LM91 derived from D39 (encapsulated), which is PspA⁻, and (4) Lyt⁻ derived from D39, unencapsulated.

Cell culture and choline binding protein purification. Cultures of 0.1 ml bacteria LM91 (−80° C. stock) were cultivated in 10 ml C+Y semisynthetic medium for 5 hours at 37° C. This 10 ml culture was then used to inoculate 400 ml C+Y, and this culture was incubated for 5 hours at 37° C. in 5% $CO_2$ to an $OD_{620}$ of 0.6. To this mixture was added 4 ml choline agarose beads (CAB), and this was incubated 30 minutes at 37° C. in 5% $CO_2$, with occasional shaking. The bacteria and beads were centrifuged at 4° C. for 15 minutes at 8000×g, and the pellet was resuspended in 50 ml rest medium (C+Y). To this 50 ml was added 20 µg/ml Leupeptin, 100 µg/ml PMSF and 250 µl Triton X100 to a final concentration of 0.5%. This mixture was rotated for 20-30 minutes until the solution became clear, indicating that all bacteria were lysed. The CAB were then washed on a glass filter with DPBS/1 M NaCl. The CAB were then incubated with 2 changes of 50 ml DPBS/1 M NaCl, and the beads were again washed on a glass filter.

Purification of choline binding proteins. Choline binding proteins (CBPs) were eluted with 3 washes of 5 ml DPBS/10% choline. The eluted CBPs were concentrated on an Ultrafree-20 concentrator (Millipore) to 1.5 ml, and then dialyzed against PBS.

Preparation of rabbit anti-CBP antiserum. Choline binding proteins isolated from the choline affinity column as described above were concentrated and used to immunize rabbits in a vaccine to generate an anti-CBP antiserum. New Zealand White rabbits were immunized by intradermal injection in the back with 500 µg purified CBPs in 1 ml of a 1:1 emulsion of buffer and Complete Freund's Adjuvant. The rabbits were boosted with a subcutaneous dorsal injection of 250 µg of purified CBPs in 1 ml of 1:1 buffer to Incomplete Freund's Adjuvant at weeks 3, 6, 9, 12, and 15. Rabbits were pre-bled, and test bled approximately 10 days prior to each boost. Serum obtained at week 16 were used in all experiments.

The CBPs were examined by SDS-PAGE and Western blot using the following antibodies: (1) polyclonal anti-pneumococcal serum (rabbit or "ROB"); (2) anti-PspA monoclonal antibody; (3) anti-FITC monoclonal antibody; (4) convalescent human anti-pneumococcal sera and (5) polyclonal anti-CBP antibody. 9 CBPs were identified on SDS-PAGE/Western blot. Results are shown in FIGS. 1 and 2.

Example 2

Characterization of Pneumoccal Choline Binding Proteins

The CBPs isolated by SDS-PAGE were subjected to N-terminal amino acid sequence analysis. The protein fraction obtained from a choline agarose column eluted from 0.5 M choline chloride was applied to an SDS polyacrylamide gel transferred to a PVDF membrane, and stained for protein. Individual bands were excised and N-terminal amino acid sequence obtained by Edman degradation. Internal sequence data was obtained from protease generated peptide fragments. Amino acid sequence data for 8 of the 9 CBPs were obtained as follows:

```
CBP112                              (SEQ ID NO: 1)
XENEGSTQAATSSNMAKTEHRKAAKQVVDE

CBP90                               (SEQ ID NO: 2)
AREFSLEKTR

CBP84                               (SEQ ID NO: 3)
XREFSLEKTRNIGIMAHVDAGKT

CBP80                               (SEQ ID NO: 4)
XKXXWQXKQYLKEDGSQAANEXVFDTA

CBP78                               (SEQ ID NO: 5)
QKIIGIDLGTTNSAVAVLEGTESKIIANPE

CBP70                               (SEQ ID NO: 6)
XXXEVAKXSQDTTTAS
```

-continued

```
CBP60                              (SEQ ID NO: 7)
XNERVKIVATLGPAVEGRG

CBP50                              (SEQ ID NO: 8)
XIIXXVYAREVLDSRGNP

CBP112-Int1                        (SEQ ID NO: 9)
EDRRNYHPTNTYK

CBP112-Int2                        (SEQ ID NO: 10)
XDDQQAEEDYA
```

None of the sequences had been previously identified, except that CBP84 was 85% identical to Elongation Factor G (EF-G) and CBP50 was similar to enolase.

Example 3

Pneumococcal Choline Binding Proteins Block Adherence

Figure 4:
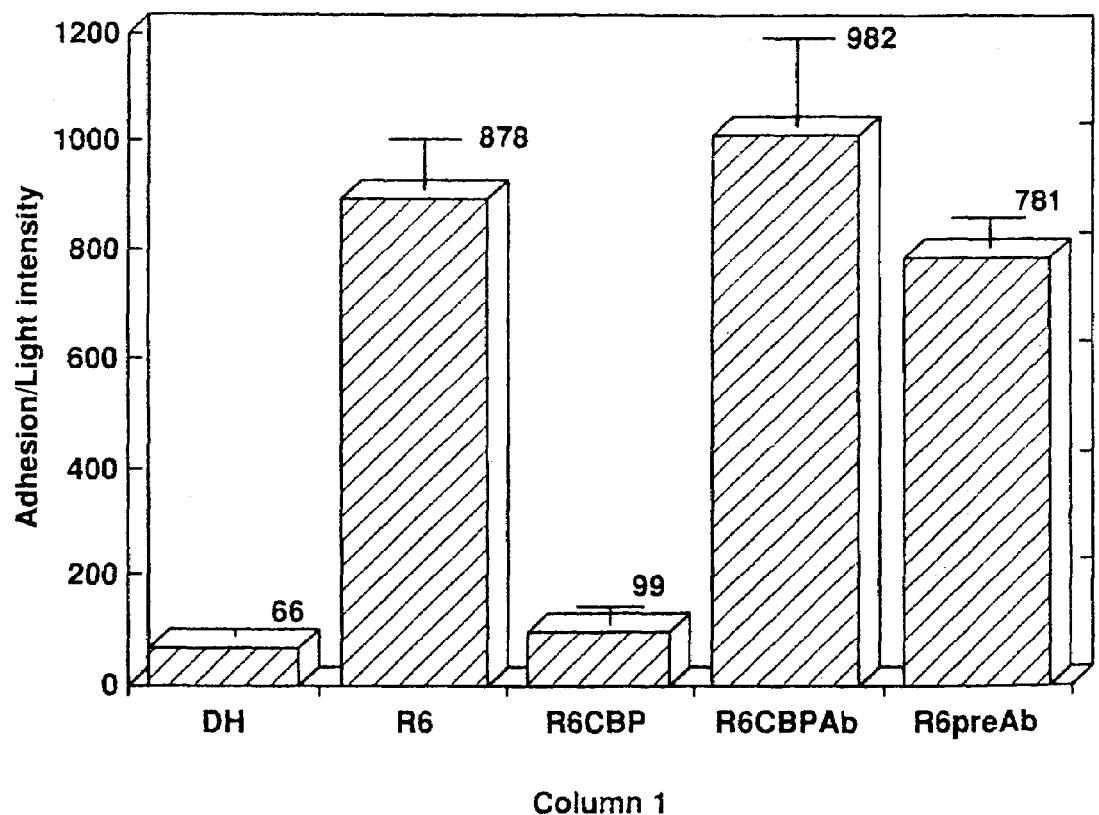
FIG. 4. Adhesion assay of PN R6 to HUVEC (endothelial) cells.

The CBP fraction isolated in Example 1 was used in an adherence assays to determine its effect on pneumococcal adherence to type II lung cells (LC) and endothelial cells of the vasculature (EC) as described in International Patent No. PCT/US95/07209, filed Jun. 6, 1995 by Tuomanen and Cundell, which is specifically incorporated herein by reference in its entirety. The CBP fraction blocked pneumococcal adherence by 45% to LC and 89% to EC in a dose-dependent manner (FIGS. 3 and 4, respectively).

Example 4

The 50 KD Choline Binding Protein Mediates Pneumococcal Adhesion

Figure 5:
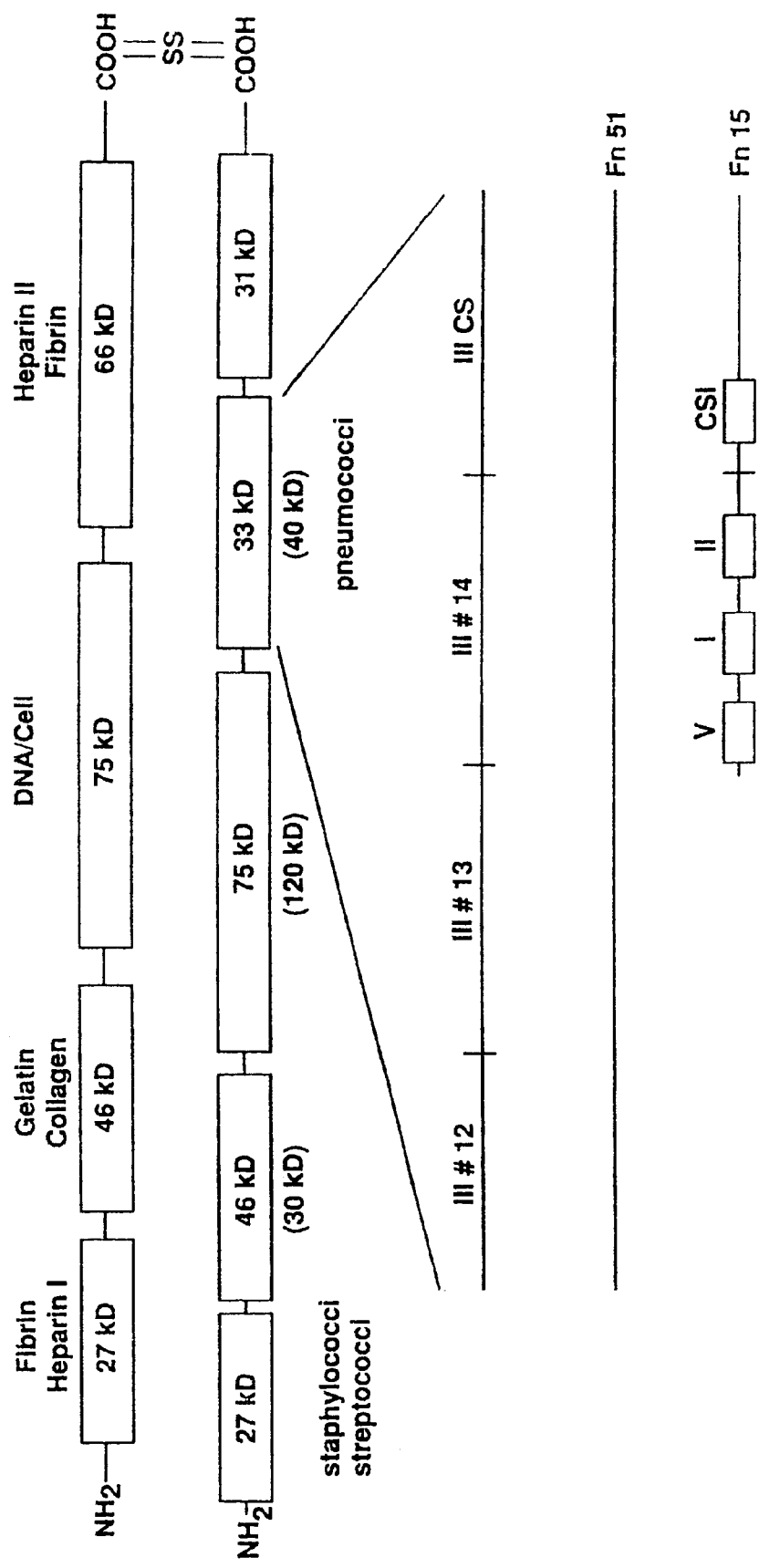
FIG. 5. PRIOR ART. Schematic drawing of fibronectin and its fragments.

Adherence to extracellular matrix proteins, such as fibronectin (see FIG. 5), affords pathogens with a means to invade injured epithelia. S. pneumoniae is known to adhere to immobilized fibronectin at a site within the C-terminal heparin binding domain [van der Flier, et. al. Infect. Immun. 63:4317-4322(1995)]. Others have reported that this region also binds the leukocyte integrin adhesion receptor α4β1. It has also been demonstrated that vascular cell adhesion molecule-1 (VCAM-1) contains sequences homologous to IIICS that are the active binding sites for α4β1. This Example evaluates, inter alia, if S. pneumoniae, like α4β1, cross-recognized fibronectin and VCAM-1.

Figure 6:
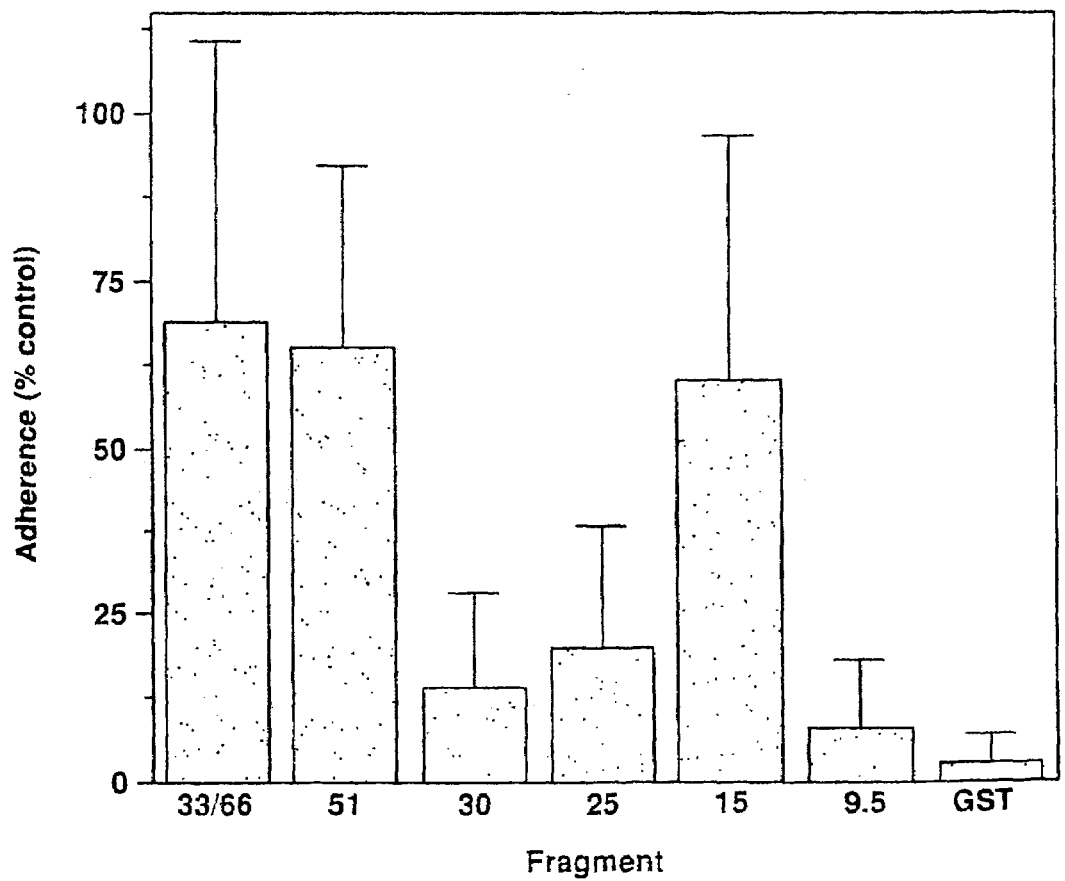
FIG. 6. Direct adherence of pneumococcus to recombinant fragments of the 33 kDa heparin 11 binding domain.
Figure 7:
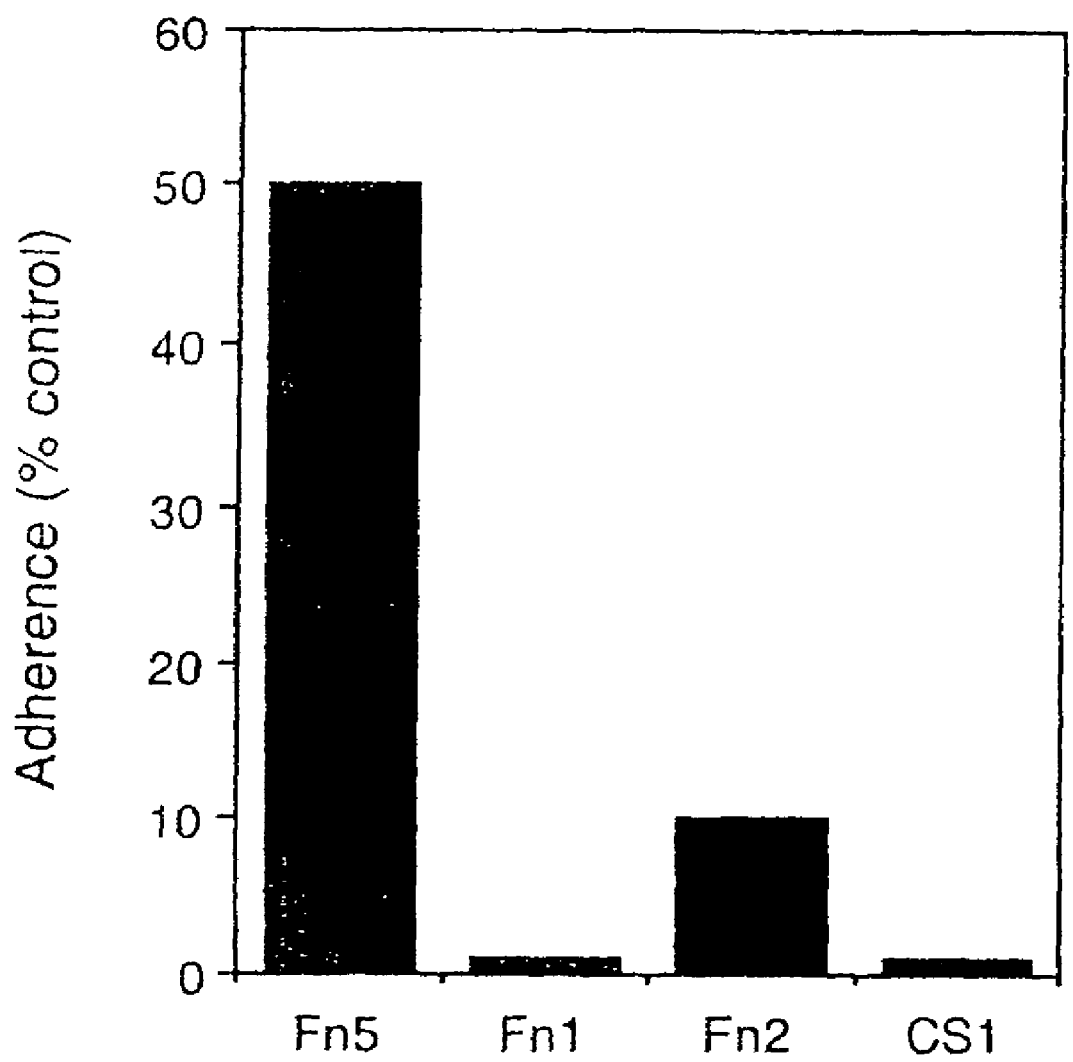
FIG. 7. Direct adherence of pneumococcus to synthetic peptides based on the heparin 11 type III #14 and IIICS regions.

Adherence of S. pneumoniae to immobilized fibronectin was inhibited 96% by preincubation of the bacteria with recombinant soluble VCAM-1. S. pneumoniae also adhered directly to VCAM-1 coated wells at a density of 75±18 bacteria/0.25 mm². This represents 6% of the adherence of pneumococci to whole fibronectin. S. pneumoniae adherence specificity was further characterized by evaluating adherence to fragments of the 33 kDa heparin binding domain of fibronectin. Various fragments of the 33 kDa domain were expressed as GST-fusion proteins. The results are shown in FIG. 6. Bacteria adhered about equally to recombinant fragments 33/66, 51, and 15. Further studies using four synthetic peptides based on the III14 region identified the peptide FN5 (WQPPRARI (SEQ ID NO:11)) as able to support adherence of S. pneumoniae (FIG. 7). Antibody to FN5 inhibited adherence of pneumococci to both whole fibronectin and VCAM-1 (92 and 69% respectively). This Example shows that S. pneumoniae binds by similar mechanisms to VCAM-1 and fibronectin, which may provide pneumococci with access to leukocyte trafficking pathways, promoting the progression of disease.

Figure 8:
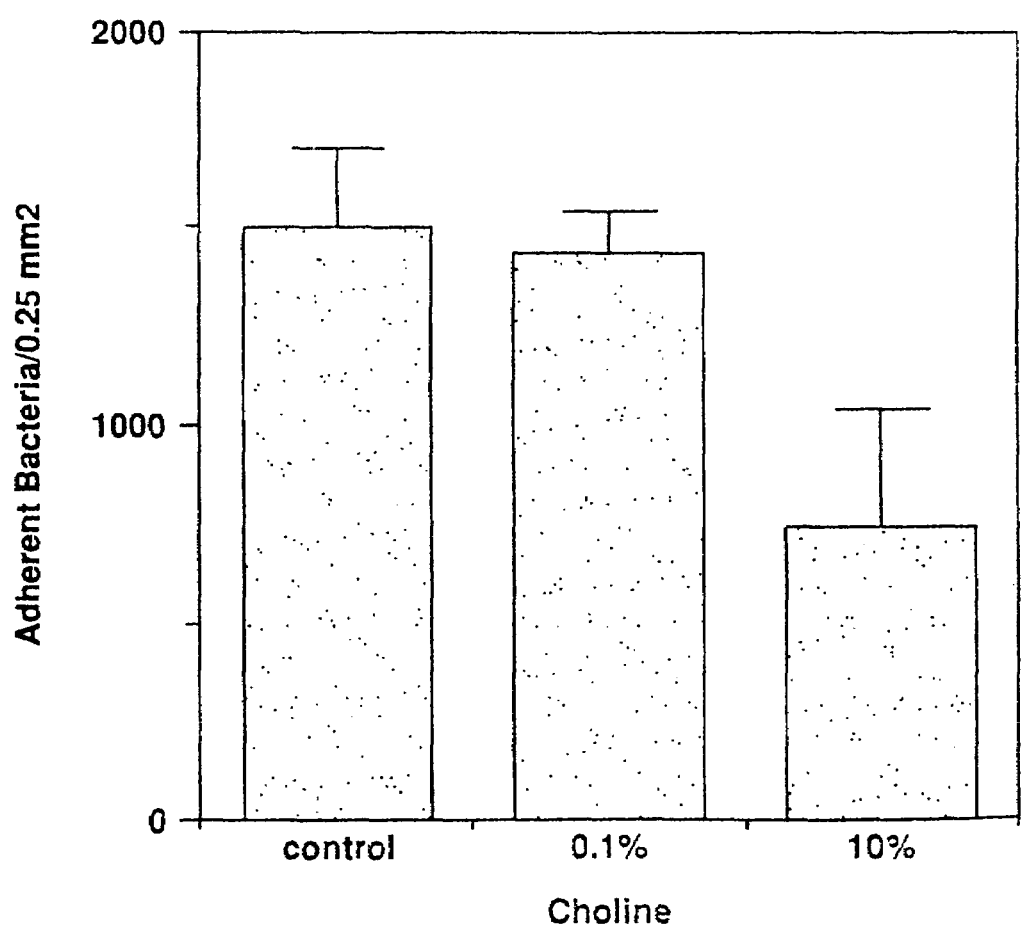
FIG. 8. Inhibition of S. pneumiae adherence by choline. Bacteria were preincubated with choline, eluted proteins and choline were washed away, and bacterial adhesion to fibronectin evaluated.
Figure 9:
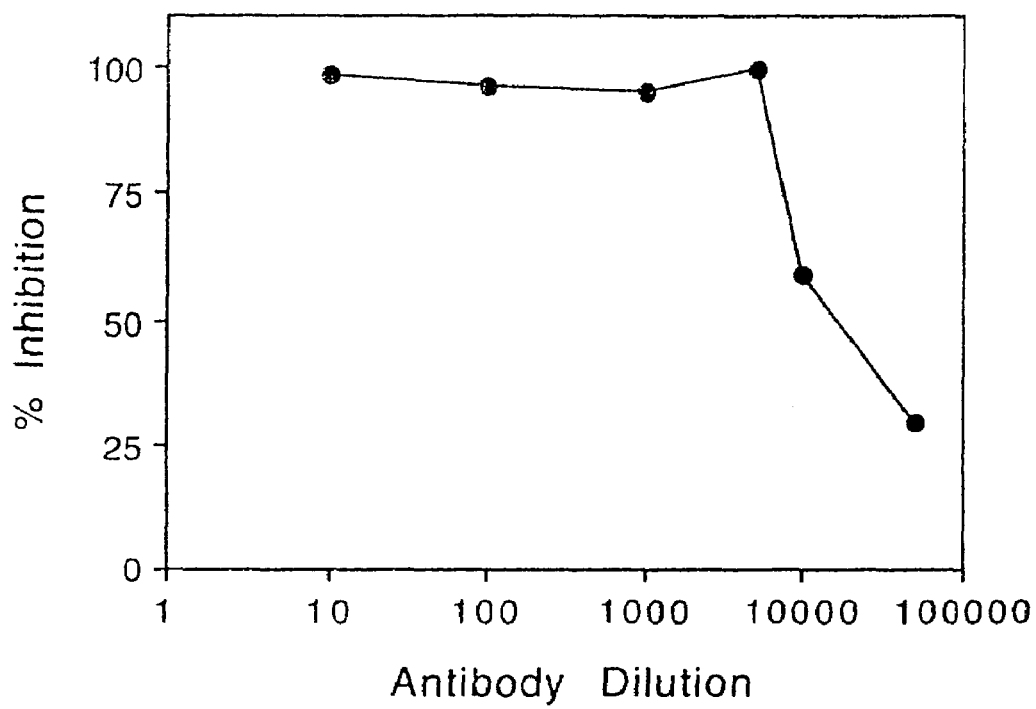
FIG. 9. Inhibition of pneumococcal adherence to fibronectin by an anti-choline antibody, TEPC15.

One adhesin on the surface of. S. pneumoniae is the 50 kDa choline binding protein. Preincubation of bacteria in a 10% choline solution, to displace surface proteins bound to choline, resulted in a greater than 50% decrease in binding of pneumococci to fibronectin (FIG. 8). Bacteria grown in the presence of ethanolamine instead of choline, so that they do not display choline binding proteins on their surfaces, failed to find to fibronectin (>85% inhibition)(data not show). Pneumococcal binding was decreased by greater than 95% by 1:10 to 1:5000 dilutions of the anti-choline antibody, TEPC15 (FIG. 9). Preparations of choline binding proteins from S. pneumoniae competitively inhibited the adherence of pneumococci to fibronectin (75-90% inhibition)(data not shown).

To confirm the identity of the protein adhesin on the surface of the pneumococcus, whole cell French Press lysates and preparations of choline binding proteins were separated by SDS-PAGE and blotted to Immobilon PVDF membranes. The membranes were then incubated with a fibronectin solution for several hours. After washing away unbound protein, bound fibronectin was detected by chemiluminescence. A band of approximately 50 kDa was observed in both the whole cell lysate and choline binding protein preparations. Amino-terminal protein sequencing of this band identified this protein as a homolog of the glycolytic enzyme, enolase (2-phospho-D-glycerate hydrolyase). In the 18 amino acid stretch analyzed by the BLAST algorithm, a 16 residue region was shown to have 93% identity (15/16) with the enolase from Bacillus subtilis (FIG. 10).

Figure 11:
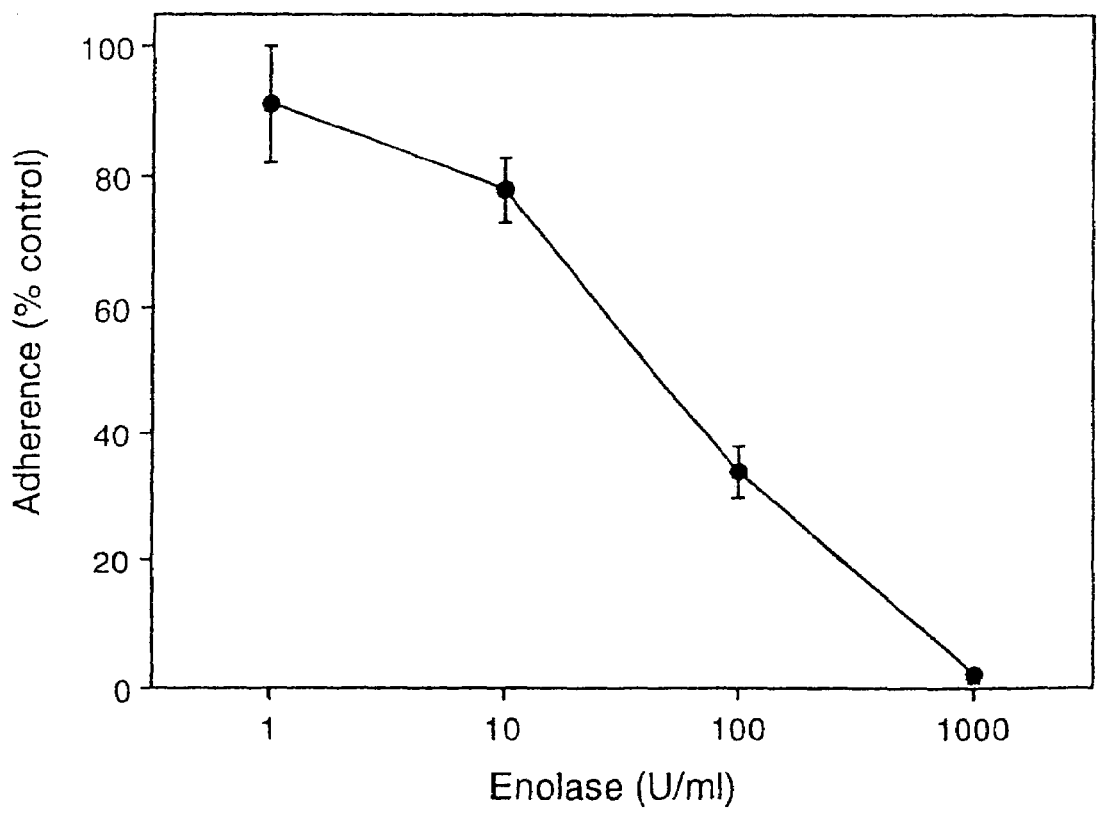
FIG. 11. Inhibition of pneumococcal adherence to fibronectin by yeast enolase (Sigma).

Addition of the glycolytic enzyme enolase (Sigma) to fibronectin coated wells prior to addition of bacteria resulted in inhibition of pneumococcal adherence to fibronectin (FIG. 11). Inhibition was dose dependent. Maximum inhibition (98%) was observed with 1000 U/ml enolase. No direct adherence of pneumococcus to enolase coated wells was observed.

Figure 12:
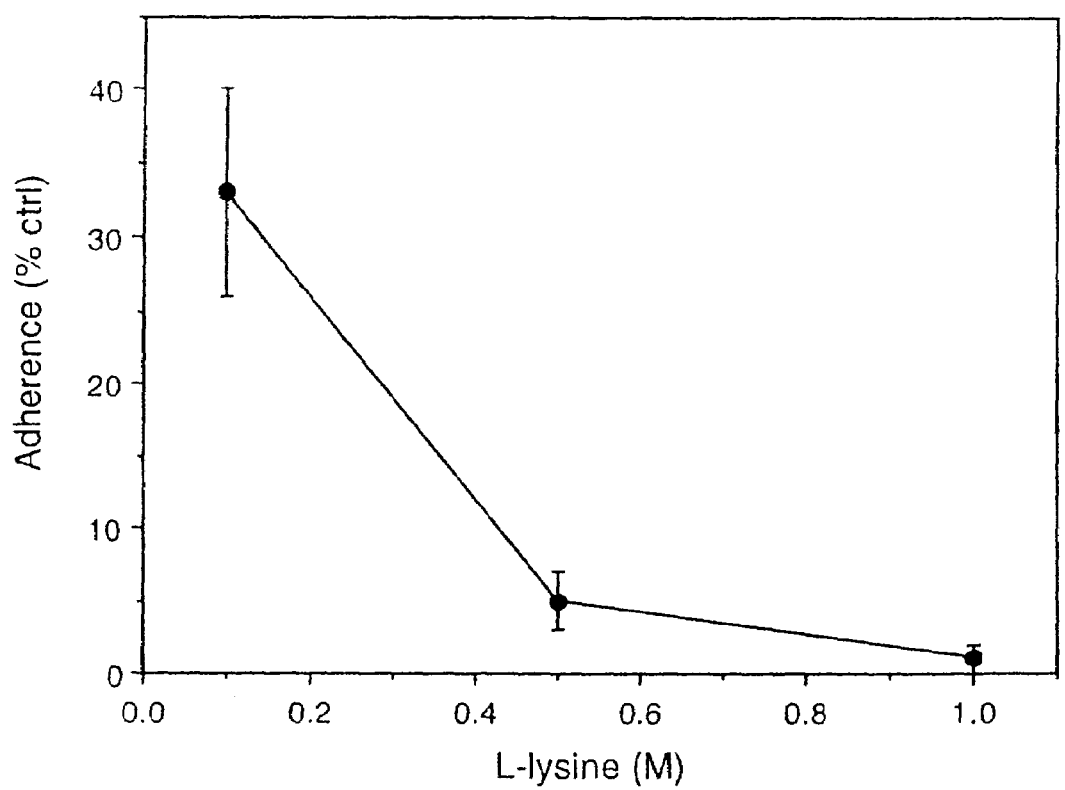
FIG. 12. Inhibition of pneumococcal adherence to fibronectin by L-lysine.

Enolase has been shown to adhere to plasminogen via its carboxy-terminal lysine residue. Adherence of S. pneumoniae to whole fibronectin is L-lysine dependent. Lysine was added to fibronectin coated wells 15 min prior to addition of bacteria. Pneumococcal adherence was inhibited 67%, 95%, and 99% by 0.1M, 0.5M, and 1M L-lysine, respectively (FIG. 12). The lysine analog, 6-amino hexanoic acid, was not able to inhibit adherence.

Figure 13:
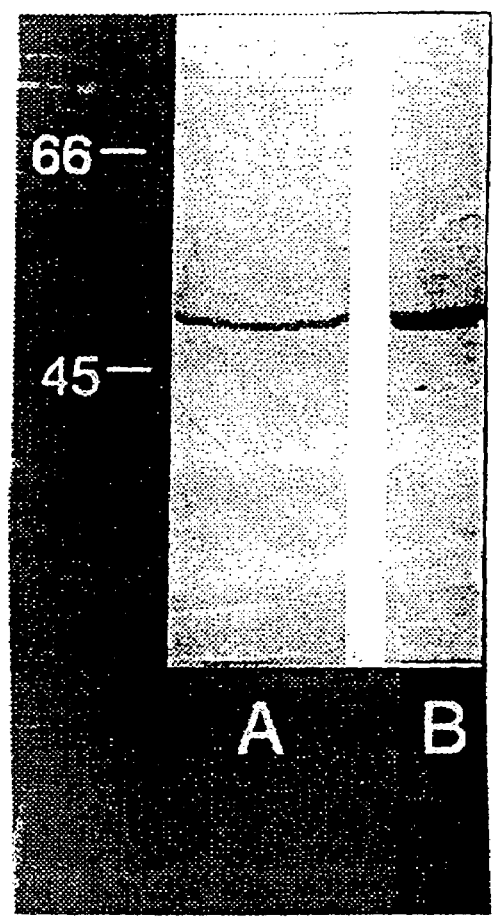
FIG. 13. SDS-PAGE of eluate from a fibronectin-coupled CnBr-activated SEPHAROSE 4B column (lane A), and yeast enolase (Sigma) (lane. B). French Press lysate of S. pneumoniae was applied to the fibronectin-SEPHAROSE column. The column was washed and adsorbed proteins eluted in 0.01, 0.1, and 0.5 M L-lysine. The 0.5 M lysine eluate was analyzed by SDS-PAGE with silver stain. The eluted protein had an apparent molecular weight comparable to yeast enolase.

S. pneumoniae French Press lysates were run over a column of fibronectin coated sepharose beads. Adherent proteins were competitively eluted with L-lysine (0.01-0.5 M) and analyzed by SDS-PAGE. A band of approximately 50 kDa was observed in all fractions (FIG. 13). This band comigrated with commercial enolase (Sigma).

Partial sequence for the enolase gene and the deduced amino acid sequence been obtained (SEQ ID NOS: 10 and 20). Comparison of the DNA and deduced amino acid sequences of pneumococcus and B. subtilis are shown in FIGS. 14 and 15, respectively. There is 74% identity at the DNA level, and 72% identity, 85% similarity, at the amino acid level. More complete sequence data for the CBP-50 enolase, lacking only a putative 42 base 5' stretch/14 amino acid N-terminal stretch are shown in SEQ ID NOS:18 and 19, respectively.

In addition to binding to fibronectin and to VCAM, the enolase homolog has two other properties related to virulence. It binds to alpha 1 acid glycoprotein (AGP) which is decorated with carbohydrates that are the key determinants of binding to activated eukaryotic cells. AGP was affixed to a column and a pneumococcal lysate was passed over the column and the proteins retained on the column were eluted. A 50 kDa protein eluted specifically and upon amino acid N-terminal sequencing was shown to be the enolase homolog. A second property of the enolase homolog is that it appears to be absent from avirulent pneumococci which have phase varied to the opaque colonial morphology. When proteins eluted from pneumococci treated with 2% choline are compared between opaque and transparent strains, the opaque are missing a 112 kDa protein and the 50 kD protein. This indicates that lack of virulence is associated with lack of expression of the enolase homolog and therefore enolase homolog is a true virulence determinant.

Materials and Methods

Bacterial strains and growth conditions. S. pneumoniae Type 2 (D39) and the isogenic, unencapsulated derivatives R6x and R6 were used. Pneumococcal strain LM34 deleted for production of pneumococcal surface protein A (pspA−) has been described [McDaniel et al., Infect. Immun., 59:222-9 (1991)]. Bacteria were grown on tryptic soy agar containing 5% sheep blood for 16-18 hours at 37° C. in 5% $CO_2$ or in a candle extinction jar.

Fibronectin and derived proteolytic fragments. Fibronectin from human plasma was purchased from Sigma (St. Louis, Mo.) and from Gibco BRL (Grand Island, N.Y.). Fragments designated by molecular size are depicted schematically in FIG. 5. Proteolytic fragments purchased from Gibco BRL (indicated in parentheses in FIG. 5) included a tryptic 30 kD collagen binding fragment, an α-chymotryptic 120 kD cell binding fragment and an α-chymotryptic 40 kD heparin binding fragment. Proteolytic fragments prepared following the method of Vercelotti et al [Vercellotti et al., J. Lab. Clin. Med., 103:34-43 (1984); McCarthy et al., 1986, supra] (indicated in the boxes in FIG. 5) included a 27 kD amino terminal fragment, a 46 kD collagen binding fragment, a 75 kD cell binding fragment, a 33 kD heparin binding fragment associated with a second 66 kD fragment (33/66 kD fragment), and a 31 kD carboxy terminal fragment. Recombinant fragments from the 33 kD domain (see FIG. 5) were prepared as described elsewhere [Huesbsch et al., Cir. Res. 77:43 (1995); Verfaille et al., Blood 84:1802 (1994)].

Binding assay to immobilized fibronectin, VCAM and fragments. Fibronectin, its recombinant fragments, or rsV-CAM were noncovalently immobilized through passive adsorption to 60 well Terasaki trays (wettable polystyrene [plasma treated], Robbins Scientific, Sunnyvale, Calif.). Briefly, substrates were reconstituted (50 mg/mg) in phosphate buffered saline (DPBS) and allowed to coat the Terasaki trays for 90 min at 37° C. The polystyrene surface was subsequently blocked with 5% bovine serum albumin (Sigma) for at least 3' hours at 37° C. Prior to use, the plates were washed five times with DPBS and excess liquid was removed from the wells. This procedure was shown to result in the preferred dense, multilayer packing of adsorbed fibronectin molecules (2.7 µg/cm$^2$) [van der Flier et al., 1995, supra].

Bacteria were labeled with fluorescein isothyocyanate as described [Geelen et al., Infect. Immun., 61:1538-1543 (1993)] and were resuspended in DPBS supplemented with 0.05% glucose and $Ca^{++}$ and $Mg^{++}$. Bacterial suspensions were brought to an $A_{620}$ of 0.04, previously established to equal 1×10$^7$ cfu/ml of S. pneumoniae. 10 µl of bacteria were added to each well and incubated statically for 1 hour at 37° C. Unbound bacteria were eliminated by washing five times with DPBS. Bound bacteria were fixed to the surface by incubation with 2.5% glutaraldehyde solution for 3 minutes. Bacteria were counted visually with an inverted microscope (Nikon) equipped for fluorescence with an IF DM 510 filter. Binding was expressed as the number of attached bacteria per 0.25 mm$^2$ surface area. Values were corrected for non-specific binding by subtracting adherence to uncoated wells and are presented as the mean±standard deviation of at least 3 experiments with 3 to 6 wells/plate/experiment. For some experiments, binding was performed in the presence of rabbit polyclonal anti-pneumococcus R6 antibody or one of the following monoclonal antibodies: anti-choline (TEPC-15), anti-PspA Xi126 and XiR278 [McDaniel et al., Microb. Pathog., 13:261-9 (1992)]; anti-pneumococcal surface adhesin A PsaA [Sampson et al., Infect. Immun., 62:319-324 (1994)]; anti-VLA-4 (R & D Systems); and anti-VCAM-1 (R & D Systems). Alternatively, potential inhibition of pneumococcal binding was assessed in the presence of purified recombinant PspA or PsaA.

Example 5

The 112 KD Choline Binding Protin, CbpA
Mediates Pneumococcal Adhesion to Human Cells In this Example, the novel 112 kDa CBP is further characterized. It functions as an adhesin, mediating adherence to cytokine activated human cells and participates in pneumococcal colonization of the nasopharynx, and is a determinant of virulence.

Using choline immobilized on a solid matrix, a family of CBPs was purified from a pspA$^-$ strain of pneumococcus. Polyclonal antibody to these CBPs passively protected mice infected intraperitoneally with a lethal challenge of pneumococci. The predominant member of this family of proteins, CbpA (or CBP-112), is a 112 kDa surface exposed protein that reacts with human convalescent sera. Sequence analysis of the corresponding gene shows a unique N-terminal sequence and a C-terminal domain comprised of 10 repeated choline binding domains similar to PspA. A cbpA defective mutant shows a greater than 50% reduction in adherence to cytokine activated human cells and failed to bind to immobilized sialic acid or laco-N-neotetraose. This mutant also shows a 100-fold reduction in virulence in an animal model for nasopharyngeal colonization. There is no difference between the parent strain and this mutant to an intraperitoneal model for sepsis. This data for CbpA extends the important functions of the CBP family to bacterial adherence and virulence and represents a new pneumococcal vaccine candidate.

Material and Methods

Strains and media. Serotype 2 S. pneumoniae strain D39, R6x (uncapsulated derivative of D39) strain SIII (capsular serotype 3) (each obtained from The Rockefeller University collection). Strain P317 is a 6B capsular serotype. A lytA deficient strain has been described [Tomasz, 1988]. LM91 was reported previously (Larry McDaniel, University of Alabama, Birmingham, Ala.). All strains were plated on tryptic soy agar supplemented with sheep blood (TSAB) to a final concentration of 3% (v/v). Cultures were grown without aeration at 37° C. in 5% $CO_2$ in a liquid semi-synthetic casein hydrolysate medium supplemented with yeast extract (C+Y medium), as described in Example 1. Pneumococci with integrated plasmids were grown in the presence of 1 mg ml$^{-1}$ erythromycin. Colony morphology was assessed on tryptic soy agar onto which 5000 U of catalase (Worthington Biochemical Co., Freehold, N.J.) were added.

Isolation of CBPs. To prepare the immobilized choline affinity matrix, vinylsulfone-activated agarose beads (1 g;

Sigma, St. Louis, Mo.) were washed twice with 10 ml of distilled water and then rotated overnight at room temperature in 10 mM choline in sodium carbonate buffer, pH 11.5. The beads were again washed with an additional 10 ml PBS to remove unbound choline.

The choline-agarose beads were added to a 400 ml culture of pneumococci ($10^8$ cfu/ml) and incubated for 30 min. The bacteria-bead complex were pelleted by centrifugation at 8000×g for 15 min, and resuspended in 50 ml C+Y medium. Bacteria were lysed with Triton X-100 (0.5%; rotation for 20 min) in the presence of leupeptin (20 mg ml$^{-1}$) and phenylmethyl-sulfonyl floride (100 mg ml$^{-1}$). The lysate was centrifuged at 1000×g for 5 min to pellet the beads. The beads were then washed with three volumes (30 ml) of phosphate buffered saline (PBS) adjusted to 0.5M NaCl, to remove any non specific bound material. Specific choline bound material was eluted with PBS adjusted to a final centration of 10% choline (w/v). This eluate was dialyzed against PBS and then passed through a Centricon 10 ultrafilter (Amicon Inc. Beverly, Mass.). The retentate contained the CBPs.

Analytical and Immunological Methods. The CBPs were analyzed by 7.5% sodium dodecyl sulfate polyacrylamide gel electrophoresis (SDS-PAGE) and by Western is blotting after electrophoretic transfer to an Immobilon-P transfer membrane (Millipore Corporation, Bedford, Mass.). For some experiments, pneumococci were labelled with fluorescein isothiocyanate (FITC) as described in the adherence assay. Western blot analysis was carried out with anti-FITC (Moleular Probes), anti-CBP or covalescent antisera each at a dilution of 1:1000. Bound antibody was detected with peroxidase conjugated goat anti-rabbit serum detected with the Chemiluminesce Kit from Amersham (Cambridge, Mass.). The convalescent sera was a mixture of sera pooled from five patients collected one month after recovery from bacteremia and pneumonia. The capsular serotypes of these infecting pneumococci were 3, 7, 14, 22, and 23.

For Western analysis of CBPs in phenotypic variants, opaque and transparent variants derived from strain R6 were grown to equal density in C+Y medium (O.D.$_{620}$ of 0.4). The cells were washed in PBS and resuspended in ¹/₂₀th the original culture volume in PBS with or without 2% choline chloride. The cells were incubated for 15 min. At 4° C. and the cell and supernatant (eluate) fractions separated. Proteins in the eluate were separated on 10% SDS-PAGE gels, transferred to Immobilon-P, and probed with the antiserum to CBPs.

To obtain primary structural information from individual CBPs, concentrated samples from the choline affinity column were applied to SDS polycryamide gel and the separated proteins transferred by electrophoresis to an Immobilon-P$^{SQ}$ transfer membrane. Proteins were identified following staining with 0.1% amido black:10% acetic acid:40% methanol. Membranes containing individually stained protein bands were excised and submitted to the Rockefeller University Protein Sequencing Center for either N-terminal or internal sequence analysis.

Preparation of rabbit anti-CBP antiserum. Antiserum was generated by HRP Inc (Denver, Pa.), according to the methods described in Example 1.

Cloning and sequencing of cbpA. DNA techniques including plasmid preparations, restriction eridonuclease digests, ligations, transformations into E. coli and gel electrophoresis were according to standard procedures known in the art.

Initial DNA sequence information for cbpA (SEQ ID NO: 24) was obtained from DNA fragments generated by anchored PCR. These fragments were generated using degenerate primers derived from the partial primary structure of internal fragments of the purified protein (SEQ ID NO: 25) purified by SDS polyacrylamide gel electrophoresis. Further sequence information was obtained from PCR generated fragments produced with templates to the end regions of the known fragments and the anchored universal primer. The polymerase chain reaction (PCR) was performed using the Gene Amp Kit (Perkin Elmer Cetus). DNA sequencing was performed on PCR fragments with an ABI373 DNA sequencer using dye labeled dideoxy terminator chemistry.

A degenerate oligonucleotide corresponding to the amino-terminal amino acid sequence (SEQ ID NO: 1) of CbpA was prepared (5'GCTCTTNCTCGATGTCTCNGTNGCCAT3'; sense) (SEQ ID NO: 22). The antisense oligonucleotide (AG-CATAGTCTTCTTCGACTTGTTGATCATC) (SEQ ID NO: 23) was prepared according to the internal amino acid sequence (SEQ ID NO: 10) that was similar to an internal sequence of PspA. LM91 total chromosomal DNA was prepared as described previously and was added (20 ng) to a PCR reaction mixture containing 1 mM each of the sense and antisense primers described above, according to the recommendations provided with AmpliTaq DNA polymerase. Thirty cycles of PCR were performed with oligonucleotide hybridization at 55° C. The DNA band at approximately 600 bp was isolated following agarose gel electrophoresis with an ultrafree-MC filter unit (0.45 mm, Millipore Corporation, Bedford, Mass.), digested with Sau3A and ligated in the BamHI site of the vector pJDC9. This mixture was transformed into E. coli DH5α and a single recombinant clone that contained the vector with the insert was identified.

Further sequence information was obtained from fragments generated by 'anchored' PCR using primers based on the ends of the known fragments and the universal primer anchored to restriction enzyme fragments of chromosomal DNA. Nucleotide sequencing was performed with an ABI 3373 DNA sequencer using dye labeled dideoxy terminator chemistry.

A cbpA deficient mutant was created by insertion duplication mutagenesis. First, a 643 base pair DNA fragment corresponding to nucleotide 554 through 1196 of cbpA was generated by the PCR. This fragment encompasses the coding region for amino acids 155 through 372. A SauIIIA digest of this fragment produced two fragments of 201 and 195 base pair which were isolated from an agarose gel, ligated into the BamHI site of pJDC9, and transformed into E. coli (DH5α). A single transformant that was transformed into the D39 or 6B strains of pneumococcus and two transformants designated SPRU625 (D39) and SPRU632 (6B) were identified that did not express CbpA by Western analysis. Southern analysis confirmed chromosomal integration of the vector disrupting cbpA in SPRU625 (Data not shown). Chromosomal DNA digested with either HindIII or EcoRV was separated by electrophoresis and, transferred bidirectionally to Hybond-N (Amersham). The membranes were probed with 643 base pair PCR fragment labeled with horseradish peroxidase (Amersham RPN 3000) as recommended by the manufacturer.

Southern analysis was carried out on electrophoretically separated chromosomal DNA digested with HindIII and EcoRV, transferred bidirectionally to Hybond-N (Amersham) and probed with the 600 bp PCR fragment labelled with horseradish peroxidase (Amersham RPN 3000) as recommended by the manufacturer.

Bacterial adhesion assay. The human Type-II lung cell line A549 (American Type Culture Collection) was cultured in Nutrient mixture F12. Ham medium (Sigma, St. Louis, Mo.) supplemented with 10% fetal calf serum (Sigma). Human umbilical vein endothelial cells (HUVEC; Clonetics, San Diego, Cailf.) were cultured in medium M199 (Sigma). At confluence, the cells were prepared for subculture with trypsin-0.05% EDTA (Sigma). For adherence assays, cells were transferred to Terasaki 60-well culture dishes (Robbins Scientific, Sunnyvale, Cailf.) and cultured for another 24 to 48 hours to form a confluent monolayer. To activate the human cells, some monblayers were incubated with TNFα (10 ng/ml for 2 hours; Boehringer-Manheim) or IL-1β (5 ng/ml for 4 hours; Sigma). Prior to the adherence assay, culture fluid was removed by washing the monolayers twice with tissue culture medium.

Bacteria at an $OD_{620}$ of 0.4 or 0.6 were washed in 1 ml carbonate buffer (0.05 M sodium carbonate, 0.1 M sodium chloride), resuspended in the same buffer and labeled with FITC (Sigma; 1 mg ml$^{-1}$) for 20 min in the dark at room temperature (LO). After 3 washes with carbonate buffer, the bacteria were resuspended in medium M199 without antibiotics and $5 \times 10^7$ pneumococci were incubated per well for 30 min at 37° C. in the presence of 5% $CO_2$. After the removal of unbound bacteria by washing the monolayers five times with M199, the cells and bacteria were fixed in 2.5% glutaraldehyde for 3 min and washed five times with PBS. Adherent pneumococci were counted visually with an inverted microscope (Diaphot-TDM; Nikon Inc., Melville, N.Y.) equipped for epifluorescence with an IF DM-510 filter and expressed as the number of attached bacteria per 100 lung cells. Values for 6-9 wells were averaged and each experiment was performed 3-6 times.

To test the ability of the mixture of CBPs to affect adherence to eucaryotic cells, the assay was modified such that monolayers were plated in 96 well dishes (Falcon) coated with 0.2% gelatin and at confluence were incubated with a range of concentrations of the mixture of CBPs (1 μg to 1 mg ml$^{-1}$) for 15 min. After washing, the CBP-treated monolayers were challenged with $5 \times 10^6$ pneumococci for 30 min, washed and adherence was quantitated as fluorescence intensity measured in a Cytofluor II (Perseptive) with excitation at 485 nm and emission at 530 nm.

Adherence to glycoconjugates was assessed by coating Terasaki plates overnight with 100 M of 6'sialyllactose-HSA, lacto-N-neotetraose-HSA, N-acetylglucosamine-β1,4-glucose-HSA or N-acetylglucosamine-β1,3-glucose-HSA (Neose Inc., Horsham, Pa.). Wells were washed and $1 \times 10^7$ FITC labelled pneumococci were added for 30 min at 37° C. Unbound cells were washed away three times with PBS and adherence was quantitated visually as described above. Each glycoconjugate was tested in 18 wells during three experiments.

Passive protection against systemic challenge. Outbred CF1 mice were housed under specific pathogen free conditions in accordance with institutional and NIH guidelines. Encapsulated pneumococci were grown for 5 hours in C+Y medium and diluted in PBS. Two groups of ten mice received an inoculum of $4.5 \times 10^4$ cfu of D39 by injection into the peritoneal cavity. One hour after bacterial challenge, one group of mice received rabbit-anti-CBP serum intraperitoneally (0.5 ml 1:10 in PBS). Control animals received pre-immune serum. A second experiment was performed at a higher challenge dose, with two groups of five mice each receiving $8.4 \times 10^4$ cfu of pneumococci. For challenge with SIII, groups of five mice received 200 cfu intraperitoneally of untreated SIII or SIII preincubated for 30 min with anti-CBP antiserum. SIII is a highly virulent strain with an $LD_{50}$ of less than 10 bacteria.

Nasopharyngeal challenge. Nasopharyngeal colonization of 1 to 5-day old Sprague-Dawley rats by pneumococci was carried out as described previously using isolates of two capsular serotypes 2 (D39) and 6B (P317). For each experiment, litters were randomized and sorted into groups ten pups per strain of pneumococci. Each pup received equal intranasal inocula of $10^4$ cfu in 10 ml of PBS of either the parent strain (D39 or P317) or the isogenic mutant containing a defined mutation in cbpA. As an additional control an isogenic strain (P354) which contains a disruption in the surface IgA1 protease gene, iga, was used. Colonization was assessed at 24 and 120 hours post-inoculation. To insure accurate evaluation of recovered bacteria, the fluid from the nasal washes were diluted in series, plated and colony counts determined. Results are expressed as the geometric mean of each group±the standard divination (n=20).

Results

Characterization of CBPs. As in Example 1, a mixture of CBPs was prepared by incubating a choline affinity matrix with a pspA deficient strain of bacteria, followed by lysis of cells, treating the beads with a high salt solution to remove non-specifically bound material and eluting the CBPs with a 10% choline solution. The CBP, LytA (muramidase), was tracked through the preparative and analytical procedures by western analysis and served as a positive control. Electrophoretic analysis of the CBP preparation showed at lease eight proteins larger than 45 kDa. A protein with an apparent molecular mass of 112 kDa was the most abundant. The muramidase, LytA, is present in the preparation with a molecular mass of 36 kDa, confirming specificity of the technique.

Figure 16A:
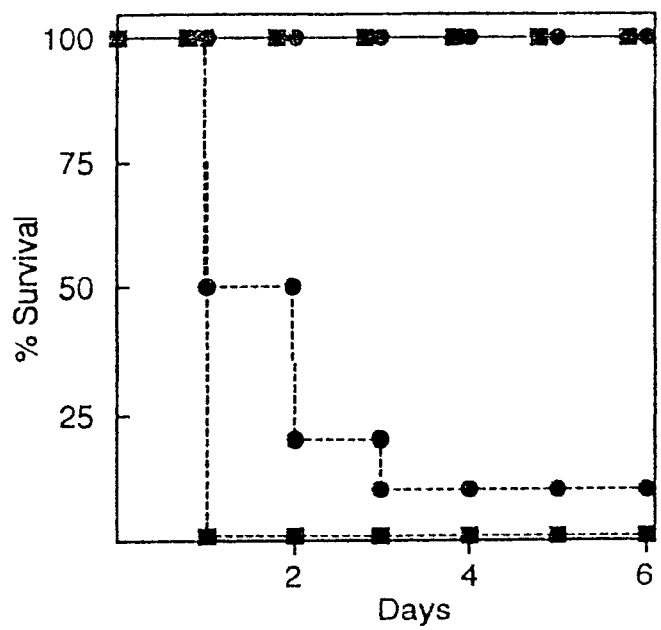
FIG. 16 Passive protection of mice against sepsis with anti-CBP antiserum. (A) CF1 mice challenged intraperitoneally with D39 (type 2) pneumococci at a dose of either $4.5 \times 10^4$ (n=10 per group; ●) or $8.4 \times 10^4$ (n=5 per group; ■) in 0.5 ml PBS. Experimental groups (-) were treated with 0.5 ml of 1:10 diluted rabbit anti-CBP serum one hour after inoculation with bacteria. Control mice (--) received pre-immune serum. Percent survival was evaluated daily over a six day period. (B) Passive protection against challenge with heterologous serotype SIII (type 3; n=5 per group; □) was performed as in A with a dose of 200 cfu. Bacteria were preincubated with antiserum (●) for 30 min prior to intraperitoneal inoculation. Blood was sampled at 24 hours for cfu and survival was assessed every 12 hours for 72 hours.
Figure 16B:
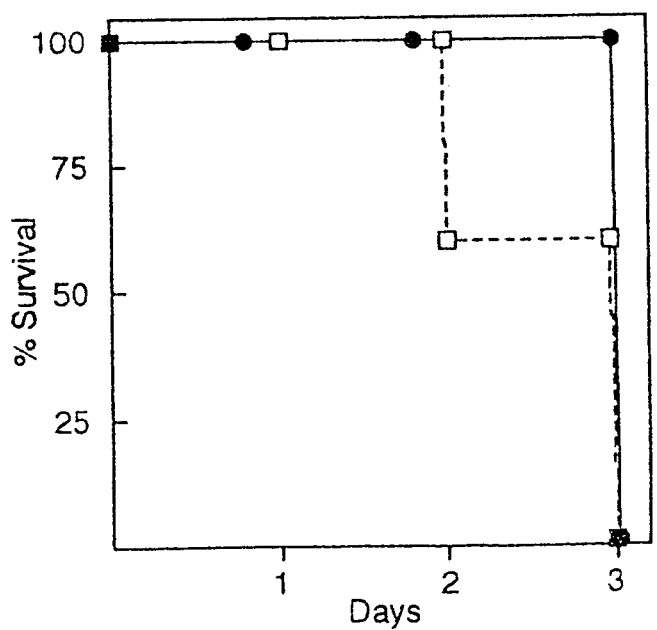
Figure 16C:
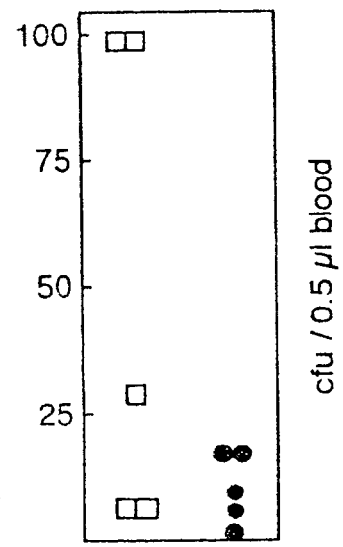

To determine whether this mixture of CBPs contained protective antigens, polyclonal antibody was raised to the CBP mixture and tested for ability to protect mice passively from intraperitoneal challenge with bacteria at a concentration 1000-fold greater than the $LD_{50}$ (FIG. 16A). Nine of ten animals receiving pre-immune serum died over 3 days in contrast with animals receiving anti-CBP antiserum. In a second experiment using a 2-fold higher inoculum, 100% of the pre-immune treated animals died over one day while all anti-CBP-treated animals survived six days. The antiserum was then tested for protection against sepsis induced by the heterologous capsule type (Type 3). All control mice receiving intraperitoneal SIII alone or SIII with pre-immune serum were bacteremic at 24 hours with a wide range of bacterial densities from $2 \times 10^4$ to $1 \times 10^7$ cfu/ml. In contrast, animals receiving SII with anti-CBP serum or anti-Type III serum showed less than $10^4$ bacteria/ml of blood. This difference was reflected in survival at 36 and 48 hours. Half of control animals died by 48 hours while none of the anti-CBP or anti-Type III antibody died during the same time interval. Protection was eventually overcome and all animals died by 72 hours regardless of treatment.

Figure 17A:
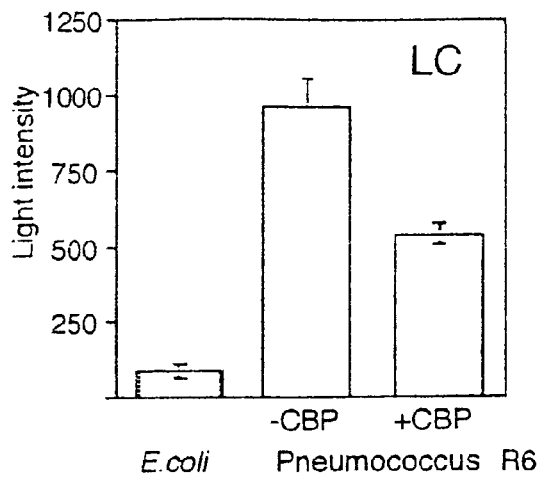
FIG. 17. Competitive inhibition of pneumococcal adherence to human cells by exogenous purified CBPs. (A) Type II lung cells (LC) or (B) endothelial cells (EC) were preincubated for 15 min with CBP preparation (1 mg/ml), washed and then incubated with FITC-labelled R6 pneumococcus. E. coli DH5a was used as a control. Adherence was quantitated by fluorescence intensity. (C) Dose dependence of the ability of CBPs to inhibit adherence of FITC-labelled pneumococci.
Figure 17B:
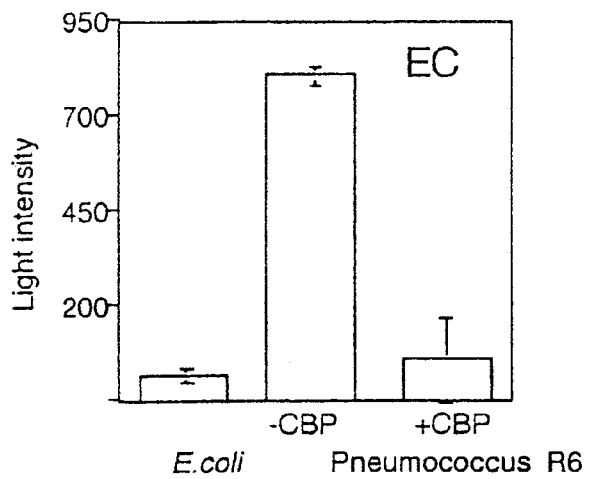
Figure 17C:
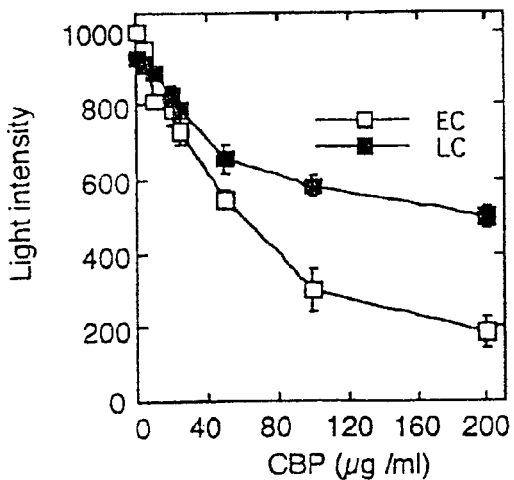

To determine if the CBP mixture might contain adhesins, the CBP mixture was tested for its ability to inhibit the adherence of pneumococcus to endothelial and epithelial cells. Pre-incubation of the eukaryotic cells with the CBPs resulted in a decrease in adherence to epithelial cells by about 50% and to endothelial cells by greater than 80% (FIG. 17A). This phenomenon was dose dependent with half maximal activity requiring approximately 60 μg/ml of CBP (FIG. 17B).

Based on the indications that the mixture of CBPs contained potential protective antigens and adhesive ligands, individual CBPs were studied further. Characteristics were sought which would be important for bioactive CBPs, specifically localization to the pneumococcal surface and reactivity with human convalescent antisera and the protective anti-CBP serum. Intact pneumococci were labelled with FITC and then subjected to CBP fractionation. SDS-PAGE and western blot analysis using anti-FITC antibody showed four proteins labelled with FITC in both whole cell preparations and CBP preparations. This is consistent with access of this group of CBPs to the pneumococcal extracellular milieu in the native bacteria. Five CBPs reacted with human convalescent antisera and the 112 kDa band was prominently labelled in preparations from whole pneumococci. This same pattern occurred using the anti-CBP antiserum, which prominently labelled the 112 kDa band in intact pneumococci and CBP preparations.

As a result of localization of the 112 kDa band to the pneumococcal surface and its strong reactivity with convalescent antisera and protective rabbit anti-CBP-sera prepared from whole bacteria or the described CBP fractionation procedure, it was determined that the 112 kDa protein is major protein component of the CBP mixture and thus designated CbpA.

Cloning and sequence analysis of cbpA. Direct N-terminal amino acid analysis of CbpA revealed a unique sequence (SEQ ID NO:1) with no similarity to proteins in any published data base. In contrast, an internal sequence (SEQ ID NO:10) was identical to an internal sequence of the CBP, PspA. Since a pspA deficient strain was used to identify cbpA, this result was not an artifact due to a genetic rearrangement of pspA but probably represented a gene composed of a unique 5' coding region and a 3' coding region similar to pspA. Using a PCR based strategy, cbpA, was cloned and sequenced. Southern analysis using a probe unique to the 5' region (see Experimental procedure section) indicated only one copy of cbpA in the LM91 chromosome (data not shown).

Analysis of the derived protein sequence of cbpA brought to light several unique properties. CpbA is a protein of 630 aa with an apparent molecular mass of 71 kDa. This is different from the calculated molecular mass (112 kDa) based on its migration properties by SDS-PAGE. The presence of a standard N-terminal signal sequence implies SecA dependant export. The protein has two distinct domains. The N-terminal region (1-340) has no obvious similarities to proteins entered into published databases. Ganier-Robson analysis predicted six alpha-helical regions from residues 10-350. Five coiled coil structures greater than 50 aa in length in this same region were predicted with the paircoil algorithm. In contrast, the C-terminal region (341-360) is nearly identical (>95%) to PspA. This similarity extends to the corresponding nucleotide sequence. Common features are a proline rich region (340-370) and ten tandem, direct repetitive sequences of 20 aa (381-584) that represent the choline binding motif that is the signature of the choline binding proteins.

Phenotypic variation and expression of the choline binding proteins. Since opaque and transparent variants of pneumococci were shown to have differences in the expression of the CBP LytA, the expression of the CBPs were compared between opaque and transparent variants of a noncapsulated strain (R6x) with anti-CBP serum. All though all bands were present in both phenotypes, several bands differed between the opaque and transparent cell types. Transparent organisms had significantly higher amounts of LytA, as previously documented. In addition, the transparent variant expressed increased amounts of CbpA and PspA. In contrast, the opaque pneumococci had more PspA. In these data minor bands between 70 and 90 kD appeared to be degradation products of PspA and CbpA. There was a protein of approximately 50 kDa present in the transparent organisms regardless of the presence of choline suggesting that this was not a CBP. As an added control, the identity of these CBPs, LytA and PspA, was confirmed by the absence of these bands in material obtained from mutants with defects in the corresponding genes (data not shown).

Functional analysis of CbpA– mutant. To asses bio activities that might be affected by CbpA, genetic mutants were constructed in a variety of assays.

The growth rates of two CbpA⁻ mutants in semisynthetic medium was equivalent to wild type and the rate of phenotypic variation from transparent to opaque colonial variants was not altered from the parental strain (data not shown). Other physiological properties of pneumococci were also unchanged, including efficiency of DNA transformation of a streptomycin resistance marker, lysis in stationary phase, and penicillin-induced lysis (data not shown).

Figure 18A:
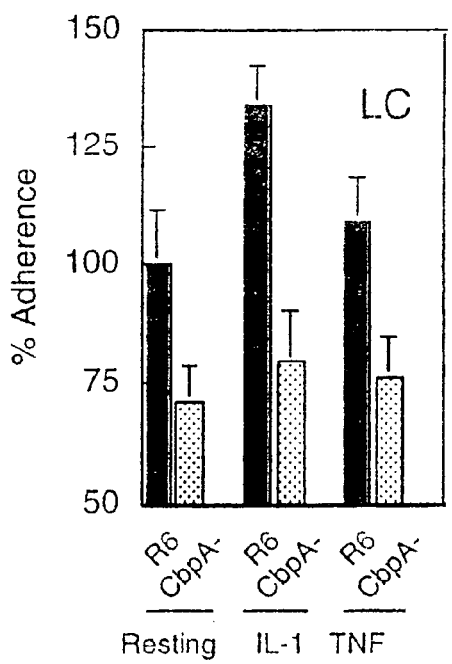
FIG. 18. Adherence of CbpA⁻ mutant to human cells and glycoconjugates. (A) Monolayers of Type II lung cell line A549 (LC) or (B) umbilical vein endothelial cells (EC) were activated by treatment with TNFα (10 ng/ml for 2 h) or IL-1 (5 ng/ml for 4 h) or were untreated (resting). R6 and the CbpA⁻ mutant were fluorescein labelled and overlaid onto the monolayers for 30 min. Nonadherent bacteria were washed away and adherence was quantitated visually and expressed as a % of control, i.e. 100%=498±81 or 174±81 R6 bacteria per 100 resting LC and EC respectively. The experiment was performed 5 times with 6-8 wells per condition. (C) Terasaki plates were coated with 6' sialyllactose (6'SL), lacto-N-neotetraose (LnNT), N-acetylgalactosamine-β1,4-galactose HSA, (GlcNAc-β1,4-Gal), N-acetylgalactosamine-β1,3-galactose HSA (GlcNAcβ1,3-Gal), or HSA at 100 μM. R6 (solid bars) or CbpA⁻ (stippled bars) were grown to an $OD_{620}$ of 0.4 for all experiments except those with 6'SL (OD620 of 0.6). Fluorescein labelled bacteria were placed in the wells for 30 min, the wells were washed, and adherent bacteria were counted visually per 40× field. Values are expressed as a % of control, i.e. 100%=133±24 R6 per 40 × field of 6'SL well, 32±8, 20±, and 15±4 for 6'SL, LnNT, GlcNAc-β1,4-gal, and GlcNAcβ1,3-Gal, respectively. The experiment was performed 3 times with 6-12 wells per condition.
Figure 18B:
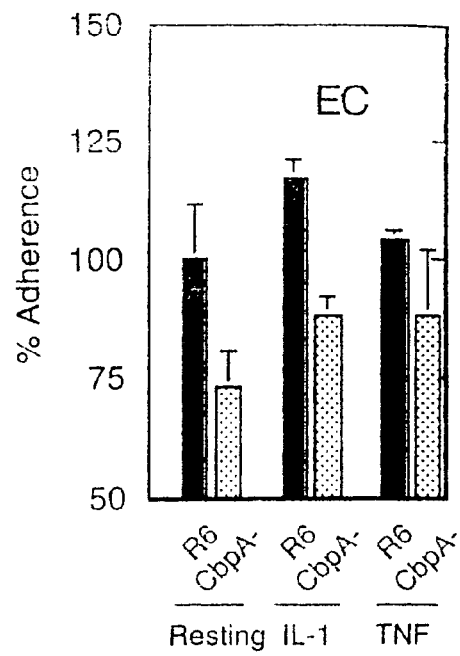

The capsular serotype 2 cbpA deficient mutant was tested for the ability to adhere to human lung epithelial cells and endothelial cells and glycoconjugates. The mutant adhered to about 80% of parental strain levels (FIG. 18A, B).

Figure 18C:
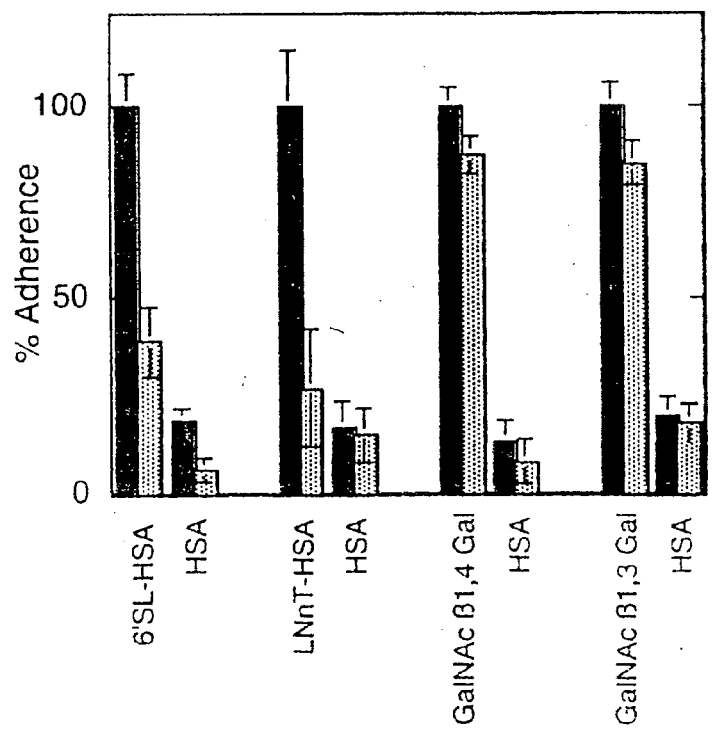

This was consistent with the equivalent ability of the two strains to adhere to immobilized GalNAc-β1,4-Gal and GalNAc-β1,3-Gal, sugars know to be receptors on these eucaryotic cells (Cundell) (FIG. 18C). A difference in adherence between the parent and mutant was detected, however, with cytokine activated cells. Adherence of the parental strain to cytokine activated cells increased to ~135% of resting cell values. In contrast, adherence of the cbpA deficient mutant failed to increase for either lung or epithelial cells (FIG. 18A). This defect in adherence to cytokine activated cells was consistent with the absense of adherence of the mutant to purified glycoconjugates (sialic acid and lacto-N-neotetraose, LnNT) known to be receptors for pneumococci on cytokine activated cells (FIG. 18C).

Figure 19:
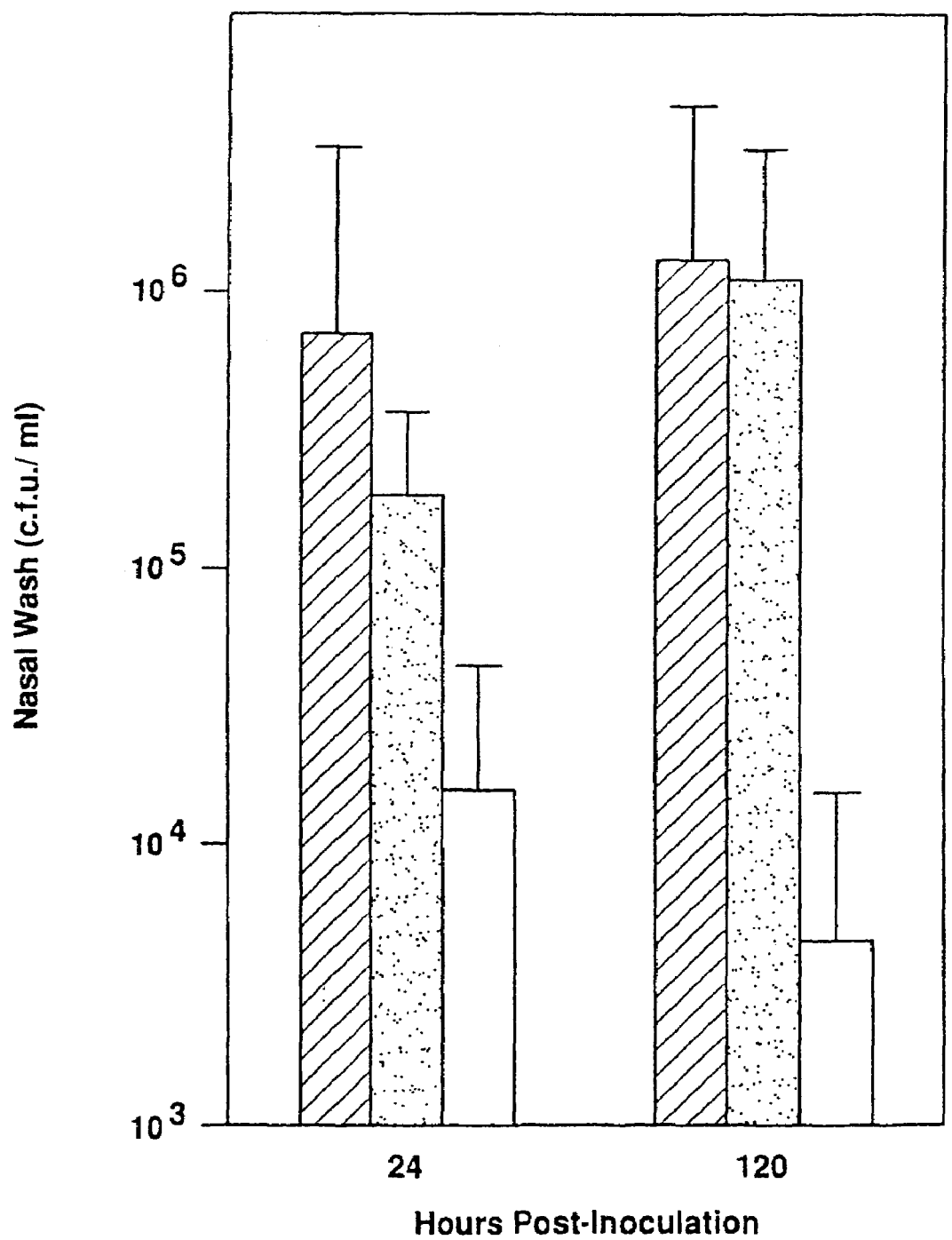
FIG. 19. The contribution of CbpA to pneumococcal carriage in infant rats. The ability to colonize the nasopharynx of 5 day old rats were compared between the control strains D39 (hatched), D39 (iga⁻) (stippled) and an isogenic cbpA deficient strain (solid). The ordinate indicates the time following inoculation and the abscissa the number of colonies in nasal washes (mean±SD, n=20 per group).

An infant rat model of pneumoccal carriage was used to determine if the ability of CbpA to mediate adherence to human epithelial cells correlated with the ability of the pneumococcus to colonize the nasopharynx. In this animal model, the pneumococcus persists on the mucosal surface at high levels for many days following a small intranasal inoculation. In contrast to the controls which were a capsular serotype 2 strain and an isogenic iga deficient mutant (IgA1 protease is another surface protein) the cbpA deficient mutant was greater than 100 fold less efficient at colonizing the infant rat nasopharynx (FIG. 19). Similar results were obtained comparing a capsular serotype 6B strain (P317) and an isogenic cbpA deficient mutant. The mean bacterial titer in nasal wash at 24 hours for animals challenged with the parental strain were $3.1 \times 10^4$ cfu/ml (n=9). In contrast, 6 of 10 pups challenged with the 6B cbpA⁻ deficient strain harbored no detectable bacteria (limit of detection 100 cfu/ml), two pups, 100 cfu/ml and 2 pups, 200 cfu/ml.

In contrast to the results obtained in the nasopharynx, no significant differences in virulence were detected in a model for pneumococcal induced sepsis with a capsular serotype 2, cbpA deficient mutant.

Discussion

To study the unique family of CBP surface proteins, a reverse genetic approach was developed whereby an immobilized choline matrix was used to selectively capture CBPs from intact pneumococci. The pspA deficient mutant LM91 was chosen as the source of CBPs to avoid purifying the gene product. Purification and electrophoretic analysis of the proteins retained on the choline matrix revealed at least eight CBPs. Several important properties of this mixture were discovered. Antiserum to the CBP mixture protected mice against challenge with the capsular serotype 2 strain from which the CBP mixture was derived. In addition, the antiserum decreased the level of bacteremia and prolonged the survival of mice challenged with a heterologous and highly virulent serotype 3 strain. Such cross protection suggests that some CBPs may share protective epitopes between serotypes.

In addition to engendering an antiserum with protective activity, the CBP mixture inhibited pneumoccal adherence when applied directly to pulmonary epithelial cells and vascular endothelial cells. These cells are in vitro models for pneumococcal adherence at sites of pneumoccal infection (NEJM). This suggested that the CBPs bound to receptors on the human cells and thereby prevented CBP mediated bacterial attachment. The demonstration of a direct CBP human cell interaction that leads to a loss of adherence distinguishes the CBPs from all other pneumoccal proteins that have been identified in genetic studies as affecting bacterial adherence. While loss of these other elements decreases the capacity of the bacteria to adhere, there is no indication that they exhibit competitive inhibition of adherence, a key characteristic of a structural adhesin. These adherence and virulence properties of the CBP mixture encouraged further analysis of individual CBPS.

CbpA was chosen for further studies because it was the most abundant CBP in the mixture, it was surface exposed and reacted strongly with both human convalescent antibody and the mouse protective anti-CBP serum, both on whole bacteria and after purification in a CBP preparation. Although the sequence predicts a molecular weight of 71 kDA, the protein migrates with an apparent mass of 112 kDa on SDS-PAGE, a discrepancy which is also characteristic of another CBP, PspA. The choline binding domains bf CbpA appears to be identical to those of PspA both at the amino acid an nucleotide level and thus chimeric gene structures for these elements. The N-terminal domains of the two CBPs are very different in primary sequence, yet they share common structural features such as several large alph-helical regions and five coiled coil regions. This would suggest that CbpA may be a fibrous protein analogous of PspA, tropomyosin, troponin, and the M protein family of streptococcal proteins. It seems reasonable that the N-terminal domain of CbpA contains one or two lectin domains capable of binding LnNT and sialic acid. Such lectin domains would be expected to remain conserved between strains and serotypes since they must retain the ability to bind the target humans glycocojugates receptors in order to retain virulence. This conservation may contribute to cross protection between various serotypes such as was observed for the anti-CBP antiserum.

CbpA appears to vary in expression coincident with the phase transition between the opaque and transparent variants. Some CBPs, such as PspA, are expressed in higher amounts in opaque variants. CbpA varies in the same manner as LytA such that transparent variants express increased amount of this protein. The significance of increased PspA in opaque organisms and the function of this CBP is unknown. In contrast the increased expression of LytA and CbpA by transparent forms correlates with increased adherence and colonization. A role for LytA in colonization could not be demonstrated. In contrast, the role of CbpA in adherence and colonization was confirmed directly by analysis of the cbpA deficient mutant.

A two step model for pneumoccal adherence has been proposed. Pneumocci initially target a niche in the host by binding surface glycoconjugates, such as GalNAc-$\beta$1,4-Gal and GalNAc-$\beta$1,3-Gal, on the surfaces of eucaryotic cells. A cbpA deficient mutant was unaffected in its adherence properties to these cells or the corresponding glycoconjugates. A second adhesive step is believed to lead to invasion and is observed upon cytokine activation of the human cell. New sugar specificities appear on the activated cells resulting in increased pneumococcal adherence. This second level of adherence is distinguished by the ability of sialyated glycoconjugates (6'SL) and LnNT to inhibit bacterial attachment. These sugars are not receptor analogs for resting cells. A cbpA deficient mutant lost the ability to bind to cytokine-activated cells or to immobilized 6'SL and LnNT. Together with the ability of purified CBPs to inhibit pneumococcal attachment, these results suggest that CbpA may be a structural adhesin with potential lectin activity. Cytokine activated cells are suggested to express the platelet activating factor (PAF) receptor which can bind the phosphorylcholine of the pneumococcal cell wall. The presence of CBPs attached to the phosphorylcholine would presumably mask phosphorylcholine binding to the PAF receptor. The relative number of free versus CBP-bound phosphorylcholine determinants on the pneumoccal surface is unknown. It appears that both CbpA and phosphorylcholine participate in pneumococcal binding to activated human cells.

CbpA appears to represent the first example of a protein adhesin on the pneumococcal surface. It may act as a bridge between cells wall phosphoorylcholine, bound by the C-terminal choline binding repeats, and human cell glycoconjugates, presumably via the N-terminal domain. The binding capacity is restricted to activated human cells and may, therefore, be important in advancing the course of disease from benign colonization to invasion. This is also consistent with results suggesting CbpA is subject to phase variation and that it is a marker for the transparent, colonization proficient, phase variants of pneumococci. Accordingly, CBPs, and CbpA (CBP-112) in particular, are attractive targets for vaccine development and passive immunotherapy.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Various references are cited throughout this specification, each of which is incorporated herein by reference in its entirety.

What is claimed is:

1. A purified antibody to an isolated streptococcal choline binding protein which choline binding protein has the following characteristics:
   a) choline-binding activity; and
   b) elution from a chromatographic column in the presence of about 10% choline;
   c) being reactive with sera from patients infected or recovering from infection with the bacteria;
   d) being labeled by flourescein isothiocyanate (FITC) without requiring *Streptococcal lysis*; and
   e) comprising an amino acid sequence selected from the group consisting of SEQ ID Nos:1,4,6,19 and 25.

2. The purified antibody of claim 1, wherein the purified antibody is a monoclonal antibody.

3. An immortal cell line that produces a monoclonal antibody according to claim 2.

4. The antibody of claim 1 or 2 labeled with a detectable label.

5. The antibody of claim 4 wherein the label is selected from the group consisting of an enzyme, a chemical which fluoresces, and a radioactive element.

6. A pharmaceutical composition comprising the antibody Of claim 1 or 2 and a pharmaceutically acceptable carrier.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
          (A) LENGTH: 30 amino acids
          (B) TYPE: amino acid
          (C) STRANDEDNESS: <Unknown>
          (D) TOPOLOGY: linear (ii) MOLECULE TYPE: peptide
          (A) DESCRIPTION: cBP112

(iii) HYPOTHETICAL: NO (iv) ANTI-SENSE: NO (xi) SEQUENCE DESCRIPTION: SEQ ID NO: 1:

Xaa Glu Asn Glu Gly Ser Thr Gln Ala Ala Thr Ser Ser Asn Met Ala
1               5                  10                  15

Lys Thr Glu His Arg Lys Ala Ala Lys Gln Val Val Asp Glu
                20                  25                  30

(2) INFORMATION FOR SEQ ID NO: 2:

(i) SEQUENCE CHARACTERISTICS:
          (A) LENGTH: 10 amino acids
          (B) TYPE: amino acid
          (C) STRANDEDNESS: <Unknown>
          (D) TOPOLOGY: linear (ii) MOLECULE TYPE: peptide
          (A) DESCRIPTION: cBP90

(iii) HYPOTHETICAL: NO (iv) ANTI-SENSE: NO (xi) SEQUENCE DESCRIPTION: SEQ ID NO: 2:

Ala Arg Glu Phe Ser Leu Glu Lys Thr Arg
1               5                  10

(2) INFORMATION FOR SEQ ID NO: 3:

(i) SEQUENCE CHARACTERISTICS:
          (A) LENGTH: 23 amino acids
          (B) TYPE: amino acid
          (C) STRANDEDNESS: <Unknown>
          (D) TOPOLOGY: linear (ii) MOLECULE TYPE: peptide
          (A) DESCRIPTION: cBP84

(iii) HYPOTHETICAL: NO (iv) ANTI-SENSE: NO (xi) SEQUENCE DESCRIPTION: SEQ ID NO: 3:

Xaa Arg Glu Phe Ser Leu Glu Lys Thr Arg Asn Ile Gly Ile Met Ala
1               5                  10                  15

His Val Asp Ala Gly Lys Thr
                20

(2) INFORMATION FOR SEQ ID NO: 4:

```
        (i) SEQUENCE CHARACTERISTICS:
            (A) LENGTH: 27 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP80

(iii) HYPOTHETICAL: NO (iv) ANTI-SENSE: NO (xi) SEQUENCE DESCRIPTION: SEQ ID NO: 4:

Xaa Lys Xaa Xaa Trp Gln Xaa Lys Gln Tyr Leu Lys Glu Asp Gly Ser
1               5                  10                  15

Gln Ala Ala Asn Glu Xaa Val Phe Asp Thr Ala
            20                  25

(2) INFORMATION FOR SEQ ID NO: 5:

(i) SEQUENCE CHARACTERISTICS:
            (A) LENGTH: 30 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP78

(iii) HYPOTHETICAL: NO (iv) ANTI-SENSE: NO (xi) SEQUENCE DESCRIPTION: SEQ ID NO: 5:

Gln Lys Ile Ile Gly Ile Asp Leu Gly Thr Thr Asn Ser Ala Val Ala
1               5                  10                  15

Val Leu Glu Gly Thr Glu Ser Lys Ile Ile Ala Asn Pro Glu
            20                  25                  30

(2) INFORMATION FOR SEQ ID NO: 6:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP70

(iii) HYPOTHETICAL: NO (iv) ANTI-SENSE: NO (xi) SEQUENCE DESCRIPTION: SEQ ID NO: 6:

Xaa Xaa Xaa Glu Val Ala Lys Xaa Ser Gln Asp Thr Thr Thr Ala Ser
1               5                  10                  15

(2) INFORMATION FOR SEQ ID NO: 7:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP60

(iii) HYPOTHETICAL: NO
```

(iv) ANTI-SENSE: NO (xi) SEQUENCE DESCRIPTION: SEQ ID NO: 7:

Xaa Asn Glu Arg Val Lys Ile Val Ala Thr Leu Gly Pro Ala Val Glu
1               5                  10                  15

Gly Arg Gly (2) INFORMATION FOR SEQ ID NO: 8:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP50 pep (iii) HYPOTHETICAL: NO (iv) ANTI-SENSE: NO (xi) SEQUENCE DESCRIPTION: SEQ ID NO: 8:

Xaa Ile Ile Xaa Xaa Val Tyr Ala Arg Glu Val Leu Asp Ser Arg Gly
1               5                  10                  15

Asn Pro (2) INFORMATION FOR SEQ ID NO: 9:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP112-Int1

(iii) HYPOTHETICAL: NO (iv) ANTI-SENSE: NO (xi) SEQUENCE DESCRIPTION: SEQ ID NO: 9:

Glu Asp Arg Arg Asn Tyr Pro Thr Asn Thr Tyr Lys
1               5                  10

(2) INFORMATION FOR SEQ ID NO: 10:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (ii) MOLECULE TYPE: peptide
            (A) DESCRIPTION: cBP112-Int2

(iii) HYPOTHETICAL: NO (iv) ANTI-SENSE: NO (xi) SEQUENCE DESCRIPTION: SEQ ID NO: 10:

Xaa Asp Asp Gln Gln Ala Glu Glu Asp Tyr Ala
1               5                  10

(2) INFORMATION FOR SEQ ID NO: 11:

(i) SEQUENCE CHARACTERISTICS:

(A) LENGTH: 8 amino acids
            (B) TYPE: amino acid
            (C) STRANDEDNESS: <Unknown>
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 11:

Trp Gln Pro Pro Arg Ala Arg Ile
1               5

(2) INFORMATION FOR SEQ ID NO: 12:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (ii) MOLECULE TYPE: peptide
            (A) DESCRIPTION: 50 KDa protein (iii) HYPOTHETICAL: NO (iv) ANTI-SENSE: NO (v) FRAGMENT TYPE: N-terminal (vi) ORIGINAL SOURCE:
            (A) ORGANISM: S. pneumoniae (xi) SEQUENCE DESCRIPTION: SEQ ID NO: 12:

Ile Thr Asp Val Tyr Ala Arg Glu Val Leu Asp Ser Arg Gly Asn Pro
1               5                   10                  15

(2) INFORMATION FOR SEQ ID NO: 13:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (ii) MOLECULE TYPE: peptide
            (A) DESCRIPTION: 50 KDa protein (iii) HYPOTHETICAL: NO (iv) ANTI-SENSE: NO (v) FRAGMENT TYPE: N-terminal (vi) ORIGINAL SOURCE:
            (A) ORGANISM: B. subtilis (xi) SEQUENCE DESCRIPTION: SEQ ID NO: 13:

Ile Val Asp Val Arg Ala Arg Glu Val Leu Asp Ser Arg Gly Asn Pro
1               5                   10                  15

(2) INFORMATION FOR SEQ ID NO: 14:

(i) SEQUENCE CHARACTERISTICS:
            (A) LENGTH: 210 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: S. pneumoniae (xi) SEQUENCE DESCRIPTION: SEQ ID NO: 14:

```
TCCCGCGGCA ACCCAACACT TGAAGTAGAA GTTTACACTG AATCAGGTGC TTTCGGACGT    60

GGTATGGTTC CATCAGGAGC TTCTACTGGT GAACACGAAG CAGTTGAACT TCGCGACGGT   120

GACAAATCTC GTTACGGTGG TCTTGGTACA CAAAAAGCTG TTGACAACGT AAACAACATC   180

ATTGCTGAGG CCATCATTGG CTACGATGTA                                    210
```

(2) INFORMATION FOR SEQ ID NO: 15:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: B. subtilis (xi) SEQUENCE DESCRIPTION: SEQ ID NO: 15:

```
TCCCGCGGCA ACCCAACAGT TGAAGTTGAA GTATATACAG AAACAGGAGC TTTCGGCCGC    60

GCATTAGTGC CAAGCGGAGC TTCTACAGGT CAATACGAAG CGGTTGAGCT TCGTGACGGC   120

GACAAAGACC GTTACCTTGG AAAAGGCGTG TTAACAGCTG TTAACAACGT AAACGAAATC   180

ATTGCTCCAG AGCTTCTTGG CTTTGATGTA                                    210
```

(2) INFORMATION FOR SEQ ID NO: 16:

(i) SEQUENCE CHARACTERISTICS:
        (A) LENGTH: 70 amino acids
        (B) TYPE: amino acid
        (C) STRANDEDNESS: <Unknown>
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: S. pneumoniae (xi) SEQUENCE DESCRIPTION: SEQ ID NO: 16:

```
Ser Arg Gly Asn Pro Thr Leu Glu Val Glu Val Tyr Thr Glu Ser Gly
 1               5                  10                  15

Ala Phe Gly Arg Gly Met Val Pro Ser Gly Ala Ser Thr Gly Glu His
                20                  25                  30

Glu Ala Val Glu Leu Arg Asp Gly Asp Lys Ser Arg Tyr Gly Gly Leu
            35                  40                  45

Gly Thr Gln Lys Ala Val Asp Asn Val Asn Asn Ile Ile Ala Glu Ala
        50                  55                  60

Ile Ile Gly Tyr Asp Val
65                  70
```

(2) INFORMATION FOR SEQ ID NO: 17:

(i) SEQUENCE CHARACTERISTICS:
        (A) LENGTH: 70 amino acids
        (B) TYPE: amino acid
        (C) STRANDEDNESS: <Unknown>
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: B. subtilis (xi) SEQUENCE DESCRIPTION: SEQ ID NO: 17:

```
Ser Arg Gly Asn Pro Thr Val Glu Val Glu Val Tyr Thr Glu Thr Gly
1               5                  10                  15

Ala Phe Gly Arg Ala Leu Val Pro Ser Gly Ala Ser Thr Gly Gln Tyr
            20                  25                  30

Glu Ala Val Glu Leu Arg Asp Gly Asp Lys Asp Arg Tyr Leu Gly Lys
        35                  40                  45

Gly Val Leu Thr Ala Val Asn Asn Val Asn Glu Ile Ile Ala Pro Glu
    50                  55                  60

Leu Leu Gly Phe Asp Val
65                  70
```

(2) INFORMATION FOR SEQ ID NO: 18:

(i) SEQUENCE CHARACTERISTICS:
        (A) LENGTH: 1511 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: S. pneumoniae (xi) SEQUENCE DESCRIPTION: SEQ ID NO: 18:

```
TCCCGCGGCA ACCCAACACT TGAAGTAGAA GTTTACACTG AATCAGGTGC TTTCGGACGT      60
GGTATGGTTC CATCAGGAGC TTCTACTGGT GAACACGAAG CAGTTGAACT TCGCGACGGT     120
GACAAATCTC GTTACGGTGG TCTTGGTACA CAAAAAGCTG TTGACAACGT AAACAACATC     180
ATTGCTGATT CTATCATTGG CTACGATGTA CGTGATCAAC AAGCTATTGA CCGTGCTATG     240
ATCGCACTTG ACGGTACTCC TAACAAAGGT AAATTGGGTG CGAATGCAAT CCTCGGTGTG     300
TCTATCGCTG TAGCTCGTGC TGCTGCTGAC TACCTTGAAA TCCCACTTTA CAGCTACCTT     360
GGTGGATTCA ACACTAAAGT TCTTCCAACT CCAATGATGA ACATCATCAA CGGTGGTTCT     420
CACTCTGACG CTCCAATCGC TTTCCAAGAG TTCATGATCT TGCCAGTTGG TGCGCCAACA     480
TTTAAAGAAA CCCTTCGTTA CGGTGCTGAA ATCTTCCACG CTCTTAAGAA ATCCTTAAA      540
TCACGTGGTT TGGAAACTGC CGTAGGTGAC GAAGGTGGAT TCGCTCCTCG TTTCGAAGGA     600
ACTGAAGATG GTGTTGAAAC TATCCTTGCT GCGATTGAAG CTGCTGGATA TGTACCAGGT     660
AAAGACGTAT TTCTCGGATT TGACTGTGCT TCATCAGAAT TCTACGATAA AGAACGTAAA     720
```

```
GTTTACGACT ACACTAAATT TGAAGGCGAA GGTGCTGCTG TTCGTACATC TGCAGAACAA      780

ATCGACTACC TTGAAGAATT GGTTAACAAA TACCCAATCA TCACTATTGA AGATGGTATG      840

GATGAAAACG ACTGGGATGG TTGGAAAGCT CTTACTGAAC GTCTTGGTAA GAAAGTACAA      900

CTTGTTGGTG ACGACTTCTT CGTAACAAAC ACTGACTACC TTGCACGTGG TATCCAAAAA      960

GGTGCTGCTA ACTCAATCCT TATCAAAGTT AACCAAATCG GTACTCTTAC TGAAACTTTT     1020

GAAGCTATCG AAATGGCTAA GAAGCTGGT TACACTGCTG TTGTATCACA CCGTTCAGGT      1080

GAAACTGAAG ATTCAACAAT CGCTGATATC GCGATTGCAA CTAACGCAGG ACAAATCAAG     1140

ACTGGTTCAC TTTCACGTAC AGACCGTATC GCTAAATACA ACCAATTGCT TCGTATCGAA     1200

GACCAACTTG GTGAAGTAGC AGAATATCGT GGATTGAAAT CATTCTACGA CCTTAAAAAA     1260

TAAAATAGTA CAGTGAACTA TTTTATCCCC GAACCATGAA ATTCAAATTC CGGCCCTTGA     1320

TTTAACAACT TTCTAGCCCC CCGATTTATC CGAGGGGATA TTTTTGTTTT AAAGGGCAAA     1380

AAGGACAAAC TTTTTAAAAT CTTTTCATAC ATTACCATAC TTGATGCTCC CCTCCTTCTT     1440

GTACTGGTTT AAGATATATAC TCCATCGATG ACACCGTCGG ATGTTAGGA TTATTCGACA      1500

ACAAGTTGAA T                                                         1511
```

(2) INFORMATION FOR SEQ ID NO: 19:

(i) SEQUENCE CHARACTERISTICS:
        (A) LENGTH: 420 amino acids
        (B) TYPE: amino acid
        (C) STRANDEDNESS: <Unknown>
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: S. pneumoniae (xi) SEQUENCE DESCRIPTION: SEQ ID NO: 19:

```
Ser Arg Gly Asn Pro Thr Leu Glu Val Glu Val Tyr Thr Glu Ser Gly
1               5                   10                  15

Ala Phe Gly Arg Gly Met Val Pro Ser Gly Ala Ser Thr Gly Glu His
            20                  25                  30

Glu Ala Val Glu Leu Arg Asp Gly Asp Lys Ser Arg Tyr Gly Gly Leu
        35                  40                  45

Gly Thr Gln Lys Ala Val Asp Asn Val Asn Asn Ile Ala Asp Ser
    50                  55                  60

Ile Ile Gly Tyr Asp Val Arg Asp Gln Gln Ala Ile Asp Arg Ala Met
65                  70                  75                  80

Ile Ala Leu Asp Gly Thr Pro Asn Lys Gly Lys Leu Gly Ala Asn Ala
                85                  90                  95

Ile Leu Gly Val Ser Ile Ala Val Ala Arg Ala Ala Asp Tyr Leu
            100                 105                 110

Glu Ile Pro Leu Tyr Ser Tyr Leu Gly Gly Phe Asn Thr Lys Val Leu
        115                 120                 125

Pro Thr Pro Met Met Asn Ile Ile Asn Gly Gly Ser His Ser Asp Ala
    130                 135                 140

Pro Ile Ala Phe Gln Glu Phe Met Ile Leu Pro Val Gly Ala Pro Thr
145                 150                 155                 160
```

```
Phe Lys Glu Thr Leu Arg Tyr Gly Ala Glu Ile Phe His Ala Leu Lys
                165                 170                 175

Lys Ile Leu Lys Ser Arg Gly Leu Glu Thr Ala Val Gly Asp Gly
            180                 185                 190

Gly Phe Ala Pro Arg Phe Glu Gly Thr Glu Asp Gly Val Glu Thr Ile
                195                 200                 205

Leu Ala Ala Ile Glu Ala Ala Gly Tyr Val Pro Gly Lys Asp Val Phe
210                 215                 220

Leu Gly Phe Asp Cys Ala Ser Ser Glu Phe Tyr Asp Lys Glu Arg Lys
225                 230                 235                 240

Val Tyr Asp Tyr Thr Lys Phe Glu Gly Glu Gly Ala Ala Val Arg Thr
                245                 250                 255

Ser Ala Glu Gln Ile Asp Tyr Leu Glu Glu Leu Val Asn Lys Tyr Pro
                260                 265                 270

Ile Ile Thr Ile Glu Asp Gly Met Asp Glu Asn Asp Trp Asp Gly Trp
                275                 280                 285

Lys Ala Leu Thr Glu Arg Leu Gly Lys Lys Val Gln Leu Val Gly Asp
290                 295                 300

Asp Phe Phe Val Thr Asn Thr Asp Tyr Leu Ala Arg Gly Ile Gln Lys
305                 310                 315                 320

Gly Ala Ala Asn Ser Ile Leu Ile Lys Val Asn Gln Ile Gly Thr Leu
                325                 330                 335

Thr Glu Thr Phe Glu Ala Ile Glu Met Ala Lys Glu Ala Gly Tyr Thr
                340                 345                 350

Ala Val Val Ser His Arg Ser Gly Glu Thr Glu Asp Ser Thr Ile Ala
                355                 360                 365

Asp Ile Ala Ile Ala Thr Asn Ala Gly Gln Ile Lys Thr Gly Ser Leu
370                 375                 380

Ser Arg Thr Asp Arg Ile Ala Lys Tyr Asn Gln Leu Leu Arg Ile Glu
385                 390                 395                 400

Asp Gln Leu Gly Glu Val Ala Glu Tyr Arg Gly Leu Lys Ser Phe Tyr
                405                 410                 415

Asp Leu Lys Lys
            420

(2) INFORMATION FOR SEQ ID NO: 20:

(i) SEQUENCE CHARACTERISTICS:
        (A) LENGTH: 429 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: S. pneumoniae (xi) SEQUENCE DESCRIPTION: SEQ ID NO: 20:

AAAAAAGGTA GCAGAAGCTG AGAAGAAGGT TGAAGAAGCT GAGAAAAAAG CCAAGGATCA      60

AAAAGAAGAA GATCGCCGTA ACTACCCAAC CAATACTTAC AAAACGCTTG ACCTTGAAAT     120

TGCTGAGTCC GATGTGAAAG TTAAGAAGGC GGAGCTTGAA CTAGTAAAAG AGGAAGCTAA     180

GGAACCTCGA GACGAGGAAA AAATTAAGCA AGCAAAAGCG AAAGTTGAGA GTAAAAAAGC     240
```

-continued

```
TGAGGCTACA AGGTTAGAAA ACATCAAGAC AGATCGTAAA AAAGCAGAAG AAGAAGCTAA    300

ACGAAAAGCA GCAGAAGAAG ATAAAGTTAA AGAAAAACCA GCTGAACAAC CACAACCAGC    360

GCCGGTTACT CAACCAGAAA AACCAGCTCC AAAACCAGAG AAGCCAGCTG AACAACCAAA    420

AGCAGAAAA                                                            429
```

(2) INFORMATION FOR SEQ ID NO: 21:

(i) SEQUENCE CHARACTERISTICS:
        (A) LENGTH: 142 amino acids
        (B) TYPE: amino acid
        (C) STRANDEDNESS: <Unknown>
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: S. pneumoniae (xi) SEQUENCE DESCRIPTION: SEQ ID NO: 21:

```
Lys Lys Val Ala Glu Ala Glu Lys Lys Val Glu Glu Ala Glu Lys Lys
1               5                   10                  15

Ala Lys Asp Gln Lys Glu Glu Asp Arg Arg Asn Tyr Pro Thr Asn Thr
            20                  25                  30

Tyr Lys Thr Leu Asp Leu Glu Ile Ala Glu Ser Asp Val Lys Val Lys
        35                  40                  45

Glu Ala Glu Leu Glu Leu Val Lys Glu Glu Ala Lys Glu Pro Arg Asp
    50                  55                  60

Glu Glu Lys Ile Lys Gln Ala Lys Ala Lys Val Glu Ser Lys Lys Ala
65                  70                  75                  80

Glu Ala Thr Arg Leu Glu Asn Ile Lys Thr Asp Arg Lys Lys Ala Glu
                85                  90                  95

Glu Glu Ala Lys Arg Lys Ala Ala Glu Glu Asp Lys Val Lys Glu Lys
            100                 105                 110

Pro Ala Glu Gln Pro Gln Pro Ala Pro Val Thr Gln Pro Glu Lys Pro
        115                 120                 125

Ala Pro Lys Pro Glu Lys Pro Ala Glu Gln Pro Lys Ala Glu
    130                 135                 140
```

(2) INFORMATION FOR SEQ ID NO: 22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(iii) HYPOTHETICAL: NO (xi) SEQUENCE DESCRIPTION: SEQ ID NO: 22:

```
GCTCTTNCTC GATGTCTCNG TNGCCAT                                         27
```

(2) INFORMATION FOR SEQ ID NO: 23:

(i) SEQUENCE CHARACTERISTICS:
        (A) LENGTH: 30 base pairs
        (B) TYPE: nucleic acid

```
            (C) STRANDEDNESS: single
            (D) TOPOLOGY: linear (ii) MOLECULE TYPE: other nucleic acid
            (A) DESCRIPTION: /desc = "oligonucleotide primer"

(iii) HYPOTHETICAL: NO (xi) SEQUENCE DESCRIPTION: SEQ ID NO: 23:

AGCATAGTCT TCTTCGACTT GTTGATCATC                                      30

(2) INFORMATION FOR SEQ ID NO: 24:

(i) SEQUENCE CHARACTERISTICS:
            (A) LENGTH: 2462 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (xi) SEQUENCE DESCRIPTION: SEQ ID NO: 24:

CCAAGCAGCC ACTTCTTCTA ATATGGCAAA GACAGAACAT AGGAAAGCTG CTAAACAAGC      60

GTCGATGAAT ATATAGAAAA AATGATGAGG GAGATTCAAC TAGATAGAAG AAAACATACC     120

CAAAATGTCG CCTTAAACAT AAAGTTGAGC GCAATTAAAA CGAAGTATTT GCGTGAATTA     180

AATGTTTTAG AAGAGAAGTC GAAAGATGAG TTGCCGTCAG AAATAAAAGC AAAGTTAGAC     240

GCAGCTTTTG AGAAGTTTAA AAAAGATACA TTGAAACCAG GAGAAAAGGT AGCAGAAGCT     300

AAGAAGAAGG TTGAAGAAGC TAAGAAAAAA GCCGAGGATC AAAAAGAAGA AGATCGTCGT     360

AACTACCCAA CCAATACTTA CAAAACGCTT GAACTTGAAA TTGCTGAGTT CGATGTGAAA     420

GTTAAAGAAG CGGAGCTTGA ACTAGTAAAA GAGGAAGCTA AGAATCTCG AAACGAGGGC      480

ACAATTAAGC AAGCAAAAGA GAAAGTTGAG AGTAAAAAAG CTGAGGCTAC AAGGTTAGAA     540

AACATCAAGA CAGATCGTAA AAAAGCAGAA GAAGAAGCTA AACGAAAAGC AGATGCTAAG     600

TTGAAGGAAG CTAATGTAGC GACTTCAGAT CAAGGTAAAC CAAAGGGGCG GGCAAAACGA     660

GGAGTTCCTG GAGAGCTAGC AACACCTGAT AAAAAGAAA ATGATGCGAA GTCTTCAGAT      720

TCTAGCGTAG GTGAAGAAAC TCTTCCAAGC TCATCCCTGA AATCAGGAAA AAAGGTAGCA     780

GAAGCTGAGA GAAGGTTGA AGAAGCTGAG AAAAAAGCCA AGGATCAAAA AGAAGAAGAT      840

CGCCGTAACT ACCCAACCAA TACTTACAAA ACGCTTGACC TTGAAATTGC TGAGTCCGAT     900

GTGAAAGTTA AGAAGCGGA GCTTGAACTA GTAAAGAGG AAGCTAAGGA ACCTCGAGAC       960

GAGGAAAAAA TTAAGCAAGC AAAAGCGAAA GTTGAGAGTA AAAAGCTGA GGCTACAAGG     1020

TTAGAAAACA TCAAGACAGA TCGTAAAAAA GCAGAAGAAG AAGCTAAACG AAAAGCAGCA    1080

GAAGAAGATA AAGTTAAAGA AAACCAGCT GAACAACCAC AACCAGCGCC GGCTACTCAA     1140

CCAGAAAAAC CAGCTCCAAA ACCAGAGAAG CCAGCTGAAC AACCAAAAGC AGAAAAAACA    1200

GATGATCAAC AAGCTGAAGA AGACTATGCT CGTAGATCAG AAGAAGAATA TAATCGCTTG    1260

ACTCAACAGC AACCGCCAAA AACTGAAAAA CCAGCACAAC CATCTACTCC AAAAACAGGC    1320

TGGAAACAAG AAAACGGTAT GTGGTACTTC TACAATACTG ATGGTTCAAT GGCAACAGGA    1380

TGGCTCCAAA ACAACGGTTC ATGGTACTAT CTAAACGCTA ATGGTGCTAT GGCGACAGGA    1440

TGGCTCCAAA ACAATGGTTC ATGGTACTAT CTAAACGCTA ATGGTTCAAT GGCAACAGGA    1500

TGGCTCCAAA ACAATGGTTC ATGGTACTAC CTAAACGCTA ATGGTGCTAT GGCGACAGGA    1560
```

```
TGGCTCCAAT ACAATGGTTC ATGGTACTAC CTAAACAGCA ATGGCGCTAT GGCGACAGGA    1620

TGGCTCCAAT ACAATGGCTC ATGGTACTAC CTCAACGCTA ATGGTGATAT GGCGACAGGA    1680

TGGCTCCAAA ACAACGGTTC ATGGTACTAC CTCAACGCTA ATGGTGATAT GGCGACAGGA    1740

TGGCTCCAAT ACAACGGTTC ATGGTATTAC CTCAACGCTA ATGGTGATAT GGCGACAGGT    1800

TGGGTGAAAG ATGGAGATAC CTGGTACTAT CTTGAAGCAT CAGGTGCTAT GAAAGCAAGC    1860

CAATGGTTCA AGTATCAGA TAAATGGTAC TATGTCAATG GCTCAGGTGC CCTTGCAGTC     1920

AACACAACTG TAGATGGCTA TGGAGTCAAT GCCAATGGTG AATGGGTAAA CTAAACCTAA    1980

TATAACTAGT TAATACTGAC TTCCTGTAAG AACTTTTTAA AGTATTCCCT ACAAATACCA    2040

TATCCTTTCA GTAGATAATA TACCCTTGTA GGAAGTTTAG ATTAAAAAAT AACTCTGTAA    2100

TCTCTAGCCG GATTTATAGC GCTAGAGACT ACGGAGTTTT TTTGATGAGG AAAGAATGGC    2160

GGCATTCAAG AGACTCTTTA AGAGAGTTAC GGGTTTTAAA CTATTAAGCC TTCTCCAATT    2220

GCAAGAGGCT TCAATCTCTG CTAGGGTGCT AGCTTGCGAA ATGGCTCCAC GGAGTTTGGC    2280

AGCGCCAGAT GTTCCACGGA GATAGTGAGG AGCGAGGCCG CGGAATTCAC GAACTGCGAC    2340

GTTTTCTCCT TTGAGGTTAA TCAATCGTTT CAAGTGTTCG TAGGCGATCT TCATCTTGTC    2400

TTCAAAGGTC AAATCAGGTA GGATTTCTCC TGTTTCAAAG TTTATGGTGG CCCTGGTTGA    2460

AG                                                                  2462

(2) INFORMATION FOR SEQ ID NO: 25:

(i) SEQUENCE CHARACTERISTICS:
        (A) LENGTH: 631 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 25:

Met Met Arg Glu Ile Gln Leu Asp Arg Arg Lys His Thr Gln Asn Val
1               5                   10                  15

Ala Leu Asn Ile Lys Leu Ser Ala Ile Lys Thr Lys Tyr Leu Arg Glu
            20                  25                  30

Leu Asn Val Leu Glu Glu Lys Ser Lys Asp Glu Leu Pro Ser Glu Ile
        35                  40                  45

Lys Ala Lys Leu Asp Ala Ala Phe Glu Lys Phe Lys Lys Asp Thr Leu
    50                  55                  60

Lys Pro Gly Glu Lys Val Ala Glu Ala Lys Lys Val Glu Glu Ala
65                  70                  75                  80

Lys Lys Lys Ala Glu Asp Gln Lys Glu Glu Asp Arg Arg Asn Tyr Pro
                85                  90                  95

Thr Asn Thr Tyr Lys Thr Leu Glu Leu Glu Ile Ala Glu Phe Asp Val
            100                 105                 110

Lys Val Lys Glu Ala Glu Leu Glu Leu Val Lys Glu Glu Ala Lys Glu
        115                 120                 125

Ser Arg Asn Glu Gly Thr Ile Lys Gln Ala Lys Glu Lys Val Glu Ser
    130                 135                 140

Lys Lys Ala Glu Ala Thr Arg Leu Glu Asn Ile Lys Thr Asp Arg Lys
145                 150                 155                 160
```

-continued

```
Lys Ala Glu Glu Glu Ala Lys Arg Lys Ala Asp Ala Lys Leu Lys Glu
                165                 170                 175

Ala Asn Val Ala Thr Ser Asp Gln Gly Lys Pro Lys Gly Arg Ala Lys
            180                 185                 190

Arg Gly Val Pro Gly Glu Leu Ala Thr Pro Asp Lys Lys Glu Asn Asp
            195                 200                 205

Ala Lys Ser Ser Asp Ser Ser Val Gly Glu Thr Leu Pro Ser Ser
    210                 215                 220

Ser Leu Lys Ser Gly Lys Lys Val Ala Glu Ala Glu Lys Lys Val Glu
225                 230                 235                 240

Glu Ala Glu Lys Lys Ala Lys Asp Gln Lys Glu Glu Asp Arg Arg Asn
                245                 250                 255

Tyr Pro Thr Asn Thr Tyr Lys Thr Leu Asp Leu Glu Ile Ala Glu Ser
            260                 265                 270

Asp Val Lys Val Lys Glu Ala Glu Leu Glu Leu Val Lys Glu Glu Ala
            275                 280                 285

Lys Glu Pro Arg Asp Glu Glu Lys Ile Lys Gln Ala Lys Ala Lys Val
    290                 295                 300

Glu Ser Lys Lys Ala Glu Ala Thr Arg Leu Glu Asn Ile Lys Thr Asp
305                 310                 315                 320

Arg Lys Lys Ala Glu Glu Ala Lys Arg Lys Ala Ala Glu Glu Asp
                325                 330                 335

Lys Val Lys Glu Lys Pro Ala Glu Gln Pro Gln Pro Ala Pro Ala Thr
            340                 345                 350

Gln Pro Glu Lys Pro Ala Pro Lys Pro Glu Lys Pro Ala Glu Gln Pro
            355                 360                 365

Lys Ala Glu Lys Thr Asp Asp Gln Gln Ala Glu Glu Asp Tyr Ala Arg
    370                 375                 380

Arg Ser Glu Glu Glu Tyr Asn Arg Leu Thr Gln Gln Pro Pro Lys
385                 390                 395                 400

Thr Glu Lys Pro Ala Gln Pro Ser Thr Pro Lys Thr Gly Trp Lys Gln
                405                 410                 415

Glu Asn Gly Met Trp Tyr Phe Tyr Asn Thr Asp Gly Ser Met Ala Thr
            420                 425                 430

Gly Trp Leu Gln Asn Asn Gly Ser Trp Tyr Tyr Leu Asn Ala Asn Gly
            435                 440                 445

Ala Met Ala Thr Gly Trp Leu Gln Asn Asn Gly Ser Trp Tyr Tyr Leu
    450                 455                 460

Asn Ala Asn Gly Ser Met Ala Thr Gly Trp Leu Gln Asn Asn Gly Ser
465                 470                 475                 480

Trp Tyr Tyr Leu Asn Ala Asn Gly Ala Met Ala Thr Gly Trp Leu Gln
                485                 490                 495

Tyr Asn Gly Ser Trp Tyr Tyr Leu Asn Ser Asn Gly Ala Met Ala Thr
            500                 505                 510

Gly Trp Leu Gln Tyr Asn Gly Ser Trp Tyr Tyr Leu Asn Ala Asn Gly
            515                 520                 525

Asp Met Ala Thr Gly Trp Leu Gln Asn Asn Gly Ser Trp Tyr Tyr Leu
    530                 535                 540

Asn Ala Asn Gly Asp Met Ala Thr Gly Trp Leu Gln Tyr Asn Gly Ser
545                 550                 555                 560

Trp Tyr Tyr Leu Asn Ala Asn Gly Asp Met Ala Thr Gly Trp Val Lys
                565                 570                 575

Asp Gly Asp Thr Trp Tyr Tyr Leu Glu Ala Ser Gly Ala Met Lys Ala
```

-continued

```
                    580                 585                 590
Ser Gln Trp Phe Lys Val Ser Asp Lys Trp Tyr Tyr Val Asn Gly Ser
        595                 600                 605

Gly Ala Leu Ala Val Asn Thr Thr Val Asp Gly Tyr Gly Val Asn Ala
    610                 615                 620

Asn Gly Glu Trp Val Asn Glx
625                 630
```